(12) United States Patent
Forsell

(10) Patent No.: US 9,839,503 B2
(45) Date of Patent: *Dec. 12, 2017

(54) IMPLANTABLE DEVICE FOR INTERNAL URINARY CONTROL

(76) Inventor: Peter Forsell, Bouveret (CH)

( * ) Notice: Subject to any disclaimer, the term of this patent is extended or adjusted under 35 U.S.C. 154(b) by 508 days.

This patent is subject to a terminal disclaimer.

(21) Appl. No.: 13/123,082

(22) PCT Filed: Oct. 9, 2009

(86) PCT No.: PCT/SE2009/051132
§ 371 (c)(1),
(2), (4) Date: Apr. 7, 2011

(87) PCT Pub. No.: WO2010/042048
PCT Pub. Date: Apr. 15, 2010

(65) Prior Publication Data
US 2011/0196194 A1    Aug. 11, 2011

Related U.S. Application Data

(60) Provisional application No. 61/227,831, filed on Jul. 23, 2009.

(30) Foreign Application Priority Data

Oct. 10, 2008 (SE) ........................ 0802154

(51) Int. Cl.
*A61F 2/00* (2006.01)
*A61M 1/00* (2006.01)
(Continued)

(52) U.S. Cl.
CPC ............ *A61F 2/0036* (2013.01); *A61F 2/042* (2013.01); *A61M 1/0023* (2013.01);
(Continued)

(58) Field of Classification Search
CPC ........ A61F 2/00; A61F 2/0004; A61F 2/0022; A61F 2/0027; A61F 2/04; A61F 2/042;
(Continued)

(56) References Cited

U.S. PATENT DOCUMENTS 4,044,401 A    8/1977 Guiset
4,634,443 A *  1/1987 Haber ............................ 600/31
(Continued)

OTHER PUBLICATIONS

International Search Report and Written Opinion of the International Searching Authority for PCT/SE2009/051132, dated Dec. 15, 2009.

*Primary Examiner* — Charles A Marmor, II
*Assistant Examiner* — Carrie R Dorna

(57) ABSTRACT

The present invention relates to an implantable apparatus for obtaining urinary control and emptying of the urinary bladder, thereby preventing from or treating involuntary urinary retention. In general terms, the apparatus comprises an expandable member adapted to be implanted inside the urinary bladder of the patient for discharging urine, and a control device for controlling the volume of the expandable member. The control device is adapted to be connected to the expandable member through the wall of the urinary bladder.

21 Claims, 14 Drawing Sheets

(51) Int. Cl.
*A61M 27/00* (2006.01)
*A61F 2/04* (2013.01)

(52) U.S. Cl.
CPC ........ *A61M 1/0072* (2014.02); *A61M 27/002* (2013.01); *A61F 2250/0001* (2013.01); *A61M 2210/1078* (2013.01)

(58) Field of Classification Search
CPC ........ A61F 2250/006; A61F 2250/0062; A61F 2250/0063; A61M 2210/1085; A61M 2210/1089; A61M 1/0072
USPC ...... 600/29–32, 37; 623/23.64, 23.65, 23.67, 623/23.68; 606/191
See application file for complete search history.

(56) References Cited

U.S. PATENT DOCUMENTS

| | | |
|---|---|---|
| 5,123,428 A | 6/1992 | Schwarz |
| 5,704,893 A * | 1/1998 | Timm .............................. 600/29 |
| 6,398,718 B1 * | 6/2002 | Yachia et al. ................... 600/29 |
| 2003/0125768 A1 | 7/2003 | Peter |
| 2003/0144648 A1* | 7/2003 | Forsell .......................... 604/544 |
| 2004/0147871 A1 | 7/2004 | Burnett |

* cited by examiner

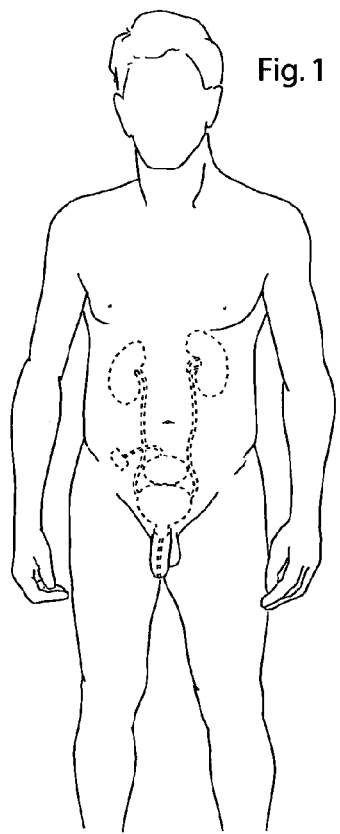
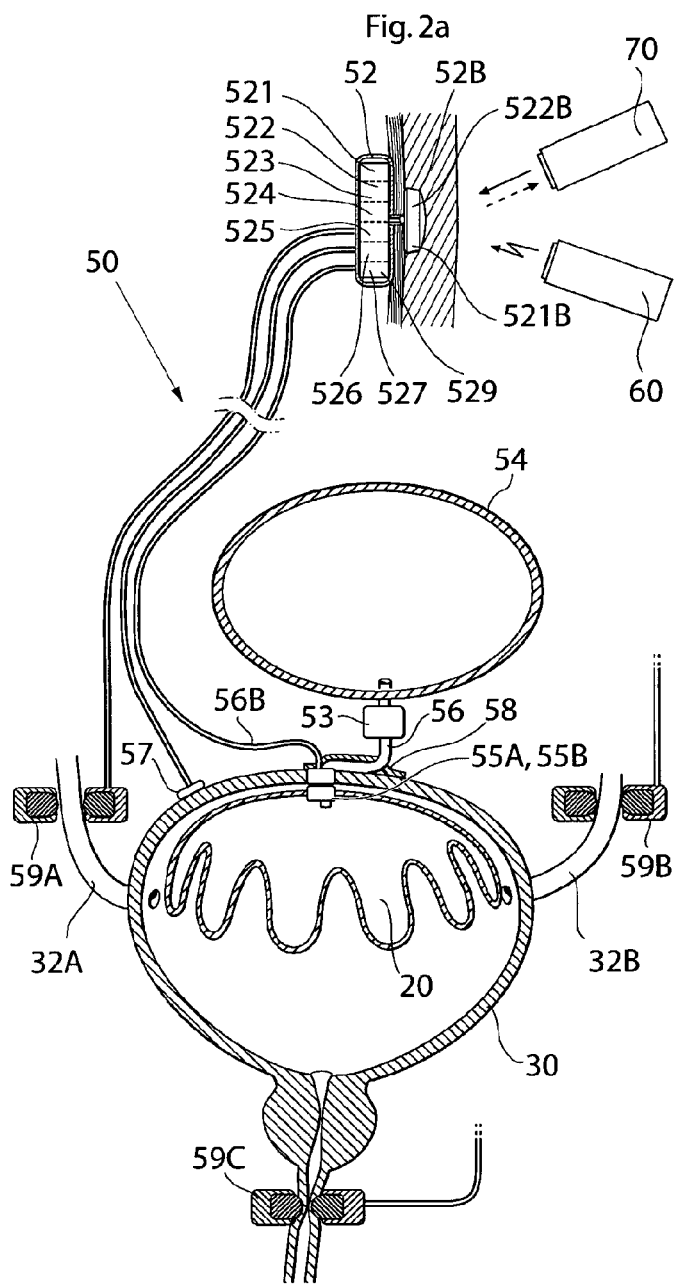
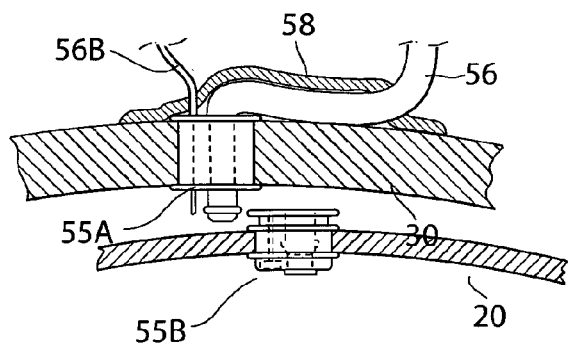

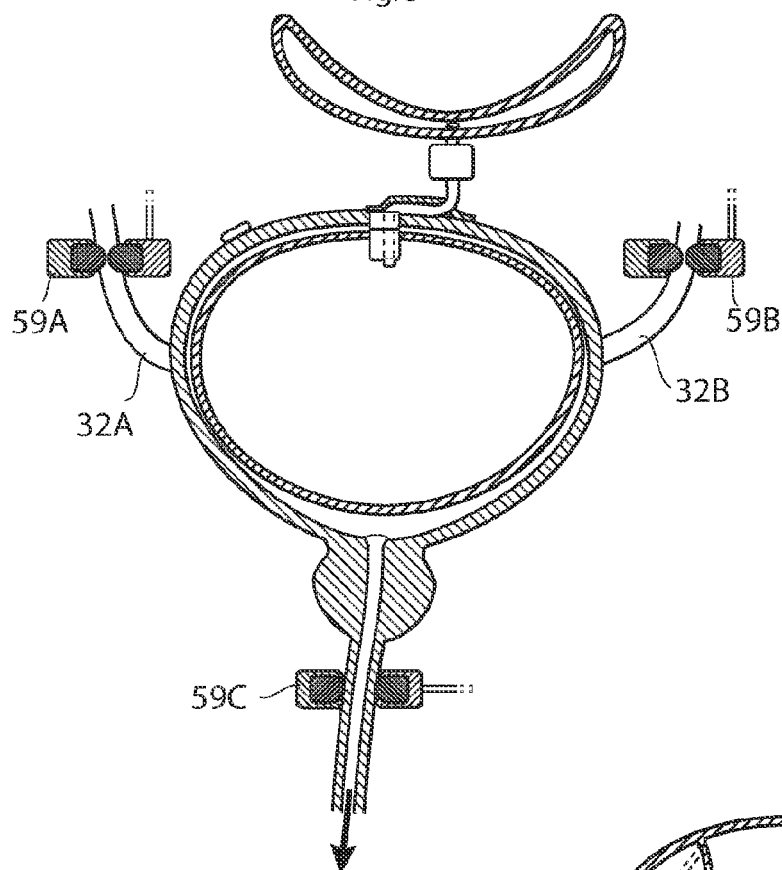
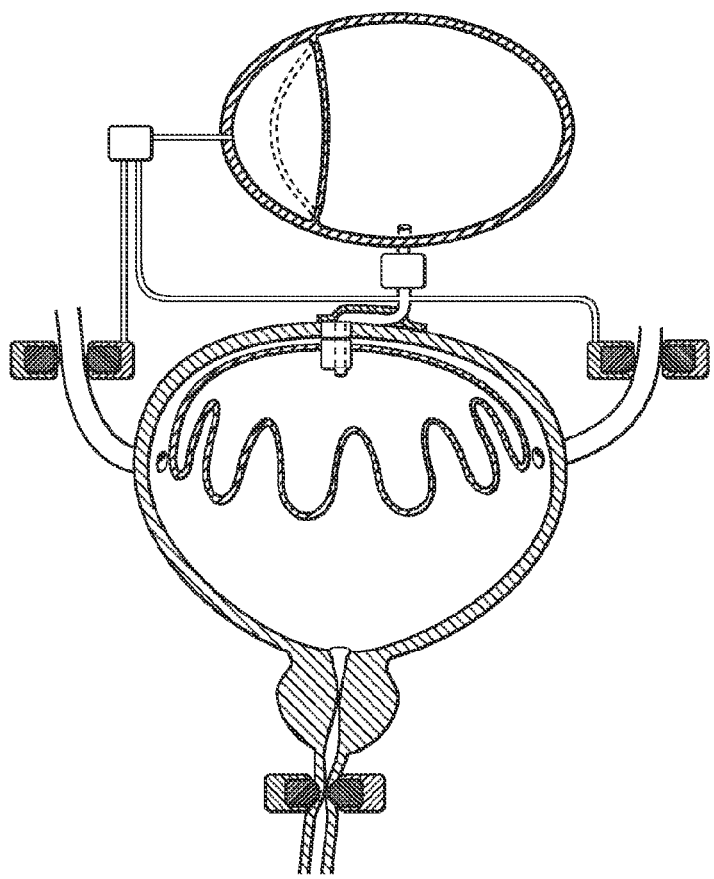

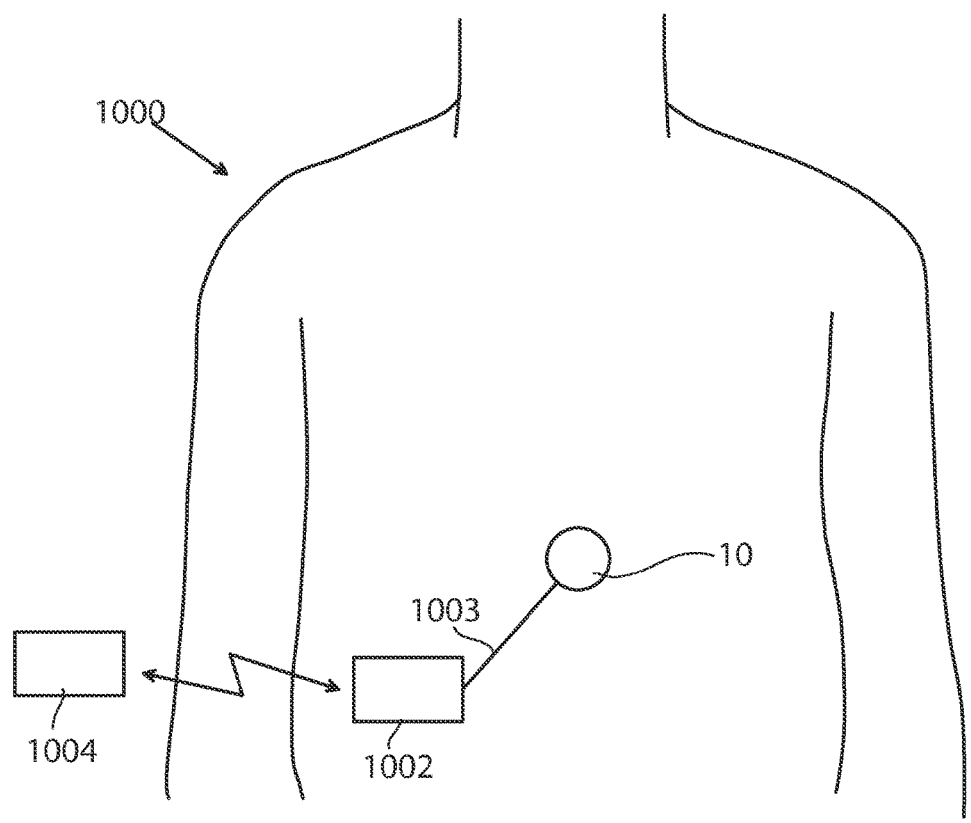

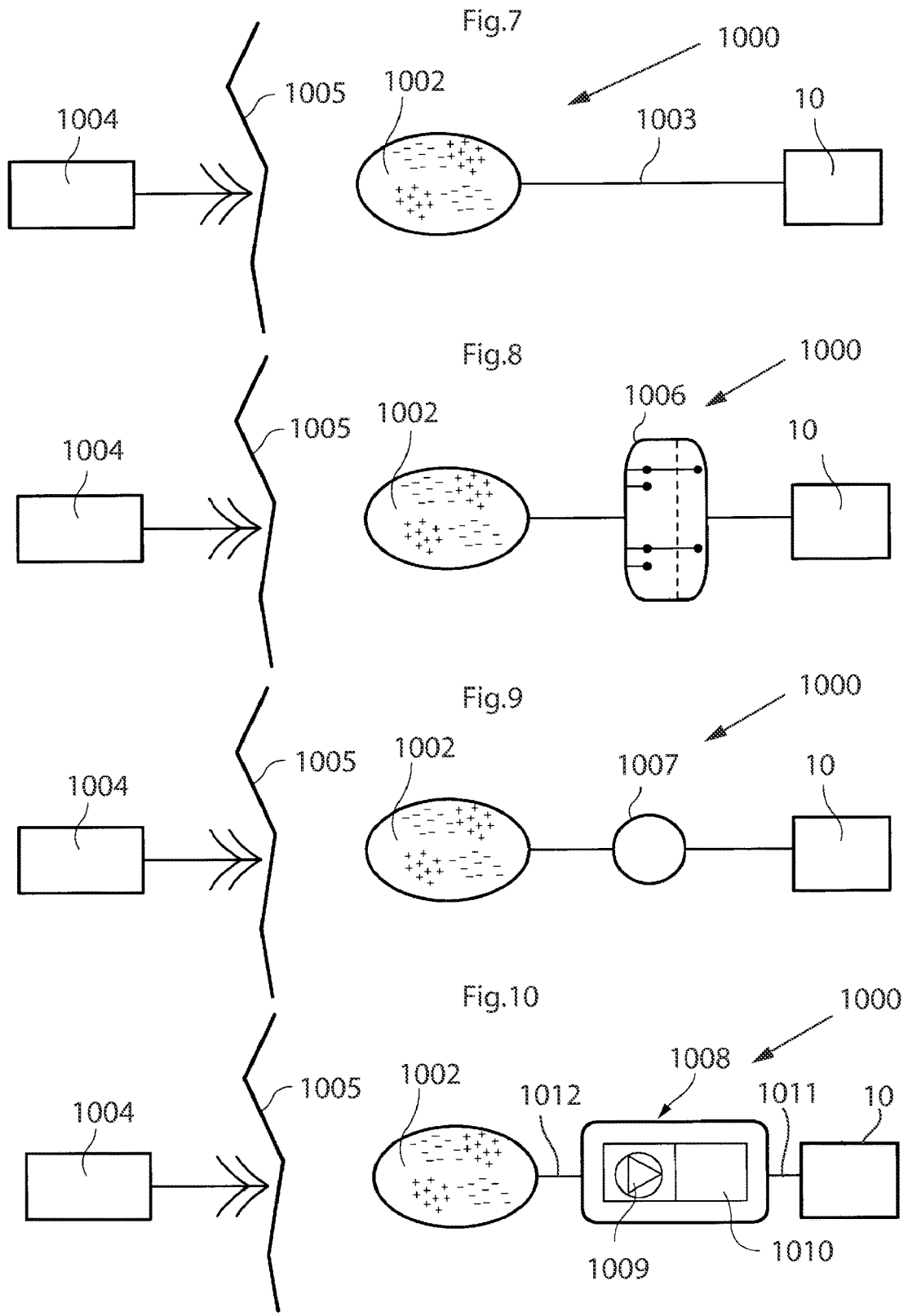

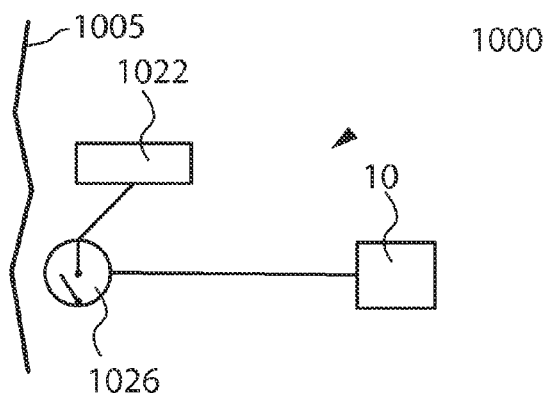
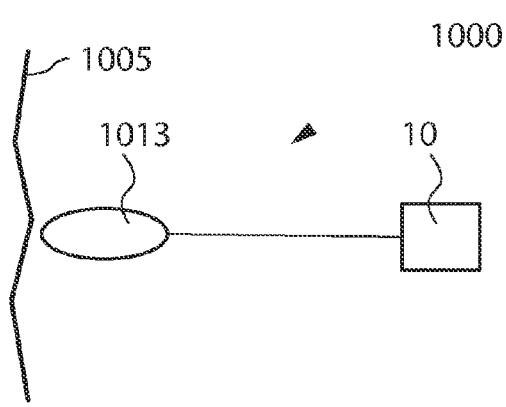
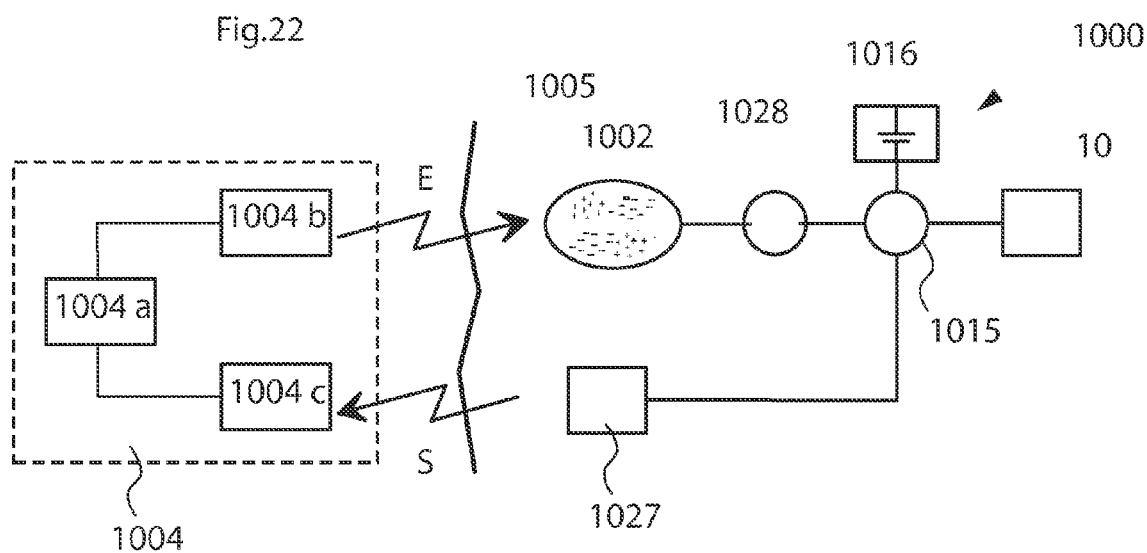

IMPLANTABLE DEVICE FOR INTERNAL URINARY CONTROL

This application is the U.S. national phase of International Application No. PCT/SE2009/051132, filed 9 Oct. 2009, which designated the U.S. and claims priority to SE Application No. 0802154-5, filed 10 Oct. 2008, and the benefit of U.S. Provisional No. 61/227,831 filed 23 Jul. 2009, the entire contents of each of which are hereby incorporated by reference.

FIELD OF INVENTION

The present invention relates to an implantable apparatus for obtaining urinary control and emptying of the urinary bladder, thereby preventing from or treating involuntary urinary retention. More particularly, the invention relates to an implantable controlled hydraulic system for discharging urine from the urinary bladder following displacement of hydraulic fluid.

BACKGROUND OF INVENTION

Urinary dysfunction commonly caused by spinal cord injuries involves involuntary urinary retention, a condition which associated with urinary infections, renal damages or damages to the urinary tract. A common treatment of urinary retention is continuous or intermittent catheterization. Besides the inconvenience for the patient, catheters always represent a risk of acquiring infections. Alternatively suggested therapies include electric stimulation of the urinary bladder for providing muscle contraction and bladder emptying (see e.g. U.S. Pat. No. 6,393,323). Electric stimulation of the bladder needs consideration to that the urinary sphincter is stimulated to contraction by electricity and pulsed stimulation will become necessary which, however, may lead to uncontrolled squirts of urine through the urethra. U.S. Pat. No. 4,044,401 discloses a totally artificial urinary bladder applied to the urethra and linked to the ureters. This artificial bladder is emptied by a manually expandable balloon. However, the subcutaneously placed reservoir of a sufficient size to empty the bladder would be unrealistically large. From this disclosure, it is evident that there is need for an implanted apparatus for a patient with an intact bladder that is convenient and compliant without any manual operations. Furthermore, such an apparatus needs to be designed with consideration to how the most exposed implanted parts shall be placed in a better way inside the body and also replaced with a minimum of intervention in the patient. The present invention intends to outline an apparatus that meets such requirements.

DESCRIPTION OF INVENTION

In general terms the present invention relates to an apparatus for treating urinary retention of a patient by discharging urine from the urinary bladder, comprising an expandable member adapted to be implanted inside the urinary bladder of the patient, and a control device for controlling the volume of the expandable member. The control device is adapted to be connected to the expandable member through the wall of the urinary bladder. As a result of the expansion of the expandable member urine is discharged from the urinary bladder through the urethra.

It will be evident from the present invention to be described as follows that the term "control device" has a meaning including both hydraulic and electric components of the apparatus assisting with the urinary discharge from the bladder. These components include both implantable components and components intended to be outside the patient's body. In this context it should be observed that the control device could be deviated into a hydraulic control device and an electric control device. The electric control device may then include power supply and electrical control functions as well as a wireless energy receiver. The external control device could also be described as the external control unit for transmitting wireless energy and receiving feedback information from implanted components. Therefore in any place in this document describing the control device this term could be replaced by any of the forgoing, whenever relevant. In one embodiment the control device comprises an internal control unit comprising at least one of a subcutaneously placed switch, an electronic circuit, a motor or a pump, wherein said internal control unit is operable from the outside of the patient's body.

The expandable member is preferably releasably attached to the control device with a detachable coupling. For this purpose the expandable member, preferably is provided with a first mating part fitting with a second mating part of the control device. The mating parts can be a combination of male/female parts which together establish a releasable detachable coupling that readily attaches or detaches the expandable member and the control device. The mating parts can together provide a snap lock coupling that simplifies the replacement of the expandable member through the urethra. However, various embodiments of mating parts that can provide a detachable coupling is conceivable in the present context, as long as they present a reliable and convenient way attaching and releasing the control device and the expandable member. Accordingly, the expandable member preferably is designed with a capacity to assume an essentially cylindrical elongated shape which admits its transportation through urethra assisted with a suitable invasive instrument. The expandable member, as inserted for implantation can comprise a bellows or a similar structure undergoing controlled expansion and collapse. Preferably, the expandable member is hydraulically controlled and comprises a cavity for hydraulic fluid and the control device comprises a bladder operating reservoir for hydraulic fluid. The expandable member and the control device are accordingly adapted to be hydraulically connected through the wall of urinary bladder. For this purpose, the control device preferably comprises a tube to establish hydraulic connection and for transporting the hydraulic fluid between the bladder operating reservoir and the cavity. The detachable coupling can in one embodiment be connectable to the hydraulic connection and its mating part establish a connection between the expandable member and the bladder operating reservoir so hydraulic fluid can be transported to and from the expandable member for discharging urine and when the urinary bladder is refilled.

The control device of the apparatus preferably comprises an operation device for transporting hydraulic fluid to and from the cavity and the bladder operating reservoir. In one mode of operation, the expandable member is adapted to be emptied by the pressure exerted by urine of the urinary bladder to transport the hydraulic fluid from the cavity to the bladder operating reservoir. The operation device is capable of transporting hydraulic fluid to cavity of the expandable member to obtain a suitable urinary pressure for discharging urine. Preferably a urinary pressure of at least 50 cm water pressure for discharging urine is obtainable.

Preferably the operation device is a powered pump. Further, the operation device can comprise or being connected to an injection port, to calibrate the amount of hydraulic fluid. The operation device can also be manually operated by an injection port which is operated from outside the body by filling or emptying said injection port.

In addition, the apparatus can comprise implantable restriction devices adapted to close the ureters when discharging, urine from the urinary bladder in order to prevent any urinary backflow towards the kidneys. The restriction devices preferably are adapted to open and close the ureters are hydraulically operable by hydraulic fluid. In a suitable embodiment the operating hydraulic fluid is displaced from the bladder operating reservoir. For this purpose, the bladder operating reservoir can comprise a sealed expandable/collapsible section for the restriction device operating hydraulic fluid. Preferably, these restriction devices open and close by the activity of the operation device.

The apparatus can also comprise a restriction device adapted to open and close the urethra to assist patients having an impaired urinary sphincter function. Restriction devices suitable for the urinary tract and wireless control of such devices are further described in European Patents Nos. EP 1253880; EP 1284691 and EP 1263355, incorporated here as references.

The control device comprises a control assembly adapted to be implanted subcutaneously or in the abdominal cavity in the patient for connection to other parts of the control device. The control assembly comprises a source of energy for powering the operation device and other energy consuming parts of the control device. These parts are further described in the context of the system according to invention comprising the recited apparatus. The control assembly can further comprise an injection port for receiving hydraulic fluid, connected to the bladder operating reservoir.

The apparatus can also comprise an implantable pressure sensor for measuring the urinary pressure in the urinary bladder direct or indirect, such as measuring the pressure inside the implantable member.

The hydraulic fluid can comprise an agent for counteracting microbial growth, such as an antibiotic.

In order to further assist urinary discharge, the control device can further comprise an implantable device for electrically stimulating muscles of the urinary bladder to contract the same, to cooperate with the expandable member to discharge urine from the urine bladder. Preferably, the electrically stimulating device comprises a plurality of electrode strips attached to muscles of the urinary bladder.

In one alternative, the apparatus can comprise a second hydraulic connection between the expandable member and the bladder operating reservoir. The second connection is dimensioned so that the pumps pumping volume capacity is significantly much larger than the emptying capacity of said second connection, when open. According to this alternative arrangement, the expandable member is adapted to be emptied by the pressure exerted by urine of the urinary bladder to transport the hydraulic fluid from the cavity to the bladder operating reservoir by said second connection. In a special embodiment, the second connection is a passageway in the detachable coupling that is established when the two mating parts are joined when bringing the expandable member together with the control device. With such an arrangement, the second connection may remain open when the main hydraulic connection is closed.

The present invention also relates to a method of implanting the described apparatus, which comprises inserting a needle-like tube into the abdomen of the patient; filling the abdomen with gas through said tube, thereby expanding the abdominal cavity; placing at least two laparoscopic trocars in the patient's body and inserting a camera through one of said trocars into the abdomen; inserting at least one dissecting tool through a trocar and dissecting an area of at least one portion of the urinary bladder of patient; incising an opening in the urinary bladder wall; placing an expandable member inside the urinary bladder; placing a control device outside the urinary bladder; and interconnecting the expandable member and the control device with an interconnection device. The method also comprises tunnelling by suturing the urinary bladder wall to itself in order to immobilize the interconnecting device in a position penetrating the urinary bladder wall, while establishing a hydraulic connection between a cavity of the expandable member and a bladder operating reservoir of the control device. Further, the method comprises placing a net adapted to support in-growth of tissue with so it at least partially covers the tunnelling.

The present invention also relates to an alternative method for implanting the apparatus that comprises the steps of cutting the skin; dissecting an area of at least one portion of the urinary bladder of patient; incising an opening in the urinary bladder wall; placing an expandable member inside the urinary bladder; placing a control device outside the urinary bladder; and interconnecting the expandable member and the control device with an interconnection device. The method further may include at least one of the following steps; placing a power source within the body for powering the control device; placing a hydraulic bladder operating reservoir and; placing a pump within the body, for pumping fluid between the bladder operating reservoir and the expandable member to discharge urine from the urine bladder.

The present invention further comprises a method of operating the apparatus that comprises activating a control assembly of the control device; increasing the volume of the expandable member; and discharging urine through the urethra. The method can further comprise the step of activating the restriction devices to temporarily close the ureters and/or a step comprising activating the restriction device to temporarily release its restriction of the urethra or the neck of the urine bladder. In the method a control assembly can receive a signal from a pressure sensor measuring the urinary pressure in the urinary bladder or expandable member. The control assembly comprises an alarm system adapted to present an alarm signal for the patient, and is able to activate said control assembly with a signal from a control unit controlled from external to the patient, such as a wireless remote control or a subcutaneously implantable switch. The method can further comprise the step of activating a pump for transporting hydraulic fluid from said bladder operating reservoir to the expandable member.

The present invention still further relates to a method of replacing an expandable member in the previous described apparatus for treating urinary retention comprising the steps of inserting an instrument adapted to operate on the expandable member through the urethra; releasing the expandable member from the control device; displacing the collapsed expandable member with the instrument; and transporting the collapsed expandable member through the urethra and out of the body. Further, the method comprises inserting a new, collapsed expandable member through the urethra; displacing the expandable member to a coupling position with the control device; and attaching the expandable member to the control device with a detachable coupling. The detachable coupling comprises two mating parts, a first mating part on the proximal part of the expandable member and a second mating part on the control device.

The present invention also relates to a system treating urinary incontinence comprising the previously described apparatus. Parts or components of system are described in the following sections of the description and should be regarded as applicable with any apparatus generally outlined in the previous part of the description.

In a preferred embodiment, the system comprises at least one switch implantable in the patient for manually and non-invasively controlling the apparatus.

In another preferred embodiment, the system comprises a wireless remote control for non-invasively controlling the apparatus. In a preferred embodiment, the system comprises a hydraulic operation device for operating the apparatus.

In one embodiment, the system comprises comprising a motor or a pump for operating the apparatus.

The system can comprise a hydraulic device having an implantable hydraulic reservoir, which is hydraulically connected to the apparatus, wherein the apparatus is adapted to be non-invasively regulated by manually pressing the hydraulic reservoir. Such a hydraulic device is intended to be linked to the control device and the expandable member of the apparatus as described in previous sections.

The system may comprise a wireless remote control for non-invasively controlling the apparatus. The wireless remote control preferably comprises at least one external signal transmitter and/or receiver, and preferably further comprises an internal signal receiver and/or transmitter implantable in the patient for receiving signals transmitted by the external signal transmitter or transmitting signals to the external signal receiver. The wireless remote control preferably transmits at least one wireless control signal for controlling the apparatus. The wireless control signal can comprise a frequency, amplitude, or phase modulated signal or a combination thereof. Alternatively, the wireless remote control transmits an electromagnetic carrier wave signal for carrying the control signal. The control signal can comprise one of the following: an electric field, a magnetic field, a combined electric and magnetic field. Alternatively, the control signal comprises an analogue signal, a digital signal, or a combination of an analogue and digital signal.

The system can further comprise a wireless energy transmission device for non-invasively energizing implantable energy consuming components of the apparatus with wireless energy. In this respect, the wireless energy can comprise a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy can comprise one of the following: an electric field, a magnetic field, a combined electric and magnetic field.

For its energizing, the system can comprise an implantable internal energy source for powering implantable energy consuming components of the apparatus. In one embodiment, an external energy source for transferring energy in a wireless mode for charging the internal energy source with energy transferred in the wireless mode. Such a system can further comprise a sensor or measuring device sensing or measuring a functional parameter correlated to the transfer of energy for charging the internal energy source, and a feedback device for sending feedback information from inside the patient's body to the outside thereof, the feedback information being related to the functional parameter sensed by the sensor or measured by the measuring device.

The system as described in any general terms can further comprise a feedback device for sending feedback information from inside the patient's body to the outside thereof, the feedback information being related to at least one of a physical parameter of the patient, such as the pressure in the urinary bladder, and a functional parameter related to the apparatus.

The system as described in any general terms can further comprise a sensor and/or a measuring device and an implantable internal control unit for controlling the apparatus in response to information being related to at least one of a physical parameter of the patient sensed by the sensor or measured by the measuring device and a functional parameter related to the apparatus sensed by the sensor or measured by the measuring device. The physical parameter is a pressure, such as the pressure in the urinary bladder or a motility movement.

The system as described in any general terms can further comprise an external data communicator and an implantable internal data communicator communicating with the external data communicator, wherein the internal communicator feeds data related to the apparatus or the patient to the external data communicator and/or the external data communicator feeds data to the internal data communicator.

In the embodiments where the system comprises an operation device for operating the apparatus, the operation device can comprise a servo designed to decrease the force needed for the operation device to operate the apparatus, so the operation device instead acts a longer way, increasing the time for a determined action.

In the embodiments where the system comprises an operation device for operating the apparatus and energy transmission device for transmitting wireless energy, such energy can be used in its wireless state to directly power the operation device to create kinetic energy for the operation of the apparatus, as the wireless energy is being transmitted by the energy-transmission device, i.e. the apparatus is directly powered.

When the system comprises a wireless energy transmission device, it can further comprises an energy-transforming device for transforming the wireless energy transmitted by the energy-transmission device from a first form into a second form energy. The energy-transforming device directly powers implantable energy consuming components of the apparatus with the second form energy, as the energy-transforming device transforms the first form energy transmitted by the energy-transmission device into the second form energy. In this respect, the second form of energy comprises at least one of a direct current, pulsating direct current and an alternating current. The so described system can comprise an implantable accumulator, wherein the second form energy is used at least partly to charge the accumulator. In general terms the energy of the first or second form comprises at least one of magnetic energy, kinetic energy, sound energy, chemical energy, radiant energy, electromagnetic energy, photo energy, nuclear energy thermal energy, non-magnetic energy, non-kinetic energy, non-chemical energy, non-sonic energy, non-nuclear energy and non-thermal energy.

The system as described in any general terms above can further comprise further comprising implantable electrical components including at least one voltage level guard and/or at least one constant current guard.

When the system comprises a wireless energy transmission device it can further comprise an external control unit for controlling the transmission of wireless energy from the energy-transmission device, and an implantable internal energy receiver for receiving the transmitted wireless energy, the internal energy receiver being connected to implantable energy consuming components of the apparatus for directly or indirectly supplying received energy thereto, the system further comprising a determination device adapted to determine an energy balance between the energy received by the internal energy receiver and the energy used for the implantable energy consuming components of the apparatus, wherein the external control unit controls the transmission of wireless energy from the external energy-transmission device, based on the energy balance determined by the determination device. In one mode, the determination device is adapted to detect a change in the energy balance, and the external control unit controls the transmission of wireless energy based on the detected energy balance change. In another mode, the determination device is adapted to detect a difference between energy received by the internal energy receiver and energy used for the implantable energy consuming components of the apparatus, and the external control unit controls the transmission of wireless energy based on the detected energy difference.

In a special embodiment, when the system comprises a wireless energy transmission device, the energy transmission device comprises a coil placed externally to the human body. The system then further comprises an implantable energy receiver to be placed internally in the human body and an electric circuit connected to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. The energy receiver receiving the transmitted wireless energy then has a varied power. In one mode, the electric circuit is adapted to deliver the electrical pulses to remain unchanged except varying the first and/or second time intervals. In another mode, the electric circuit has a time constant and is adapted to vary the first and second time intervals only in the range of the first time constant, so that when the lengths of the first and/or second time intervals are varied, the transmitted power over the coil is varied.

Embodiments of the system including a feedback device, as described above, can further comprise an implantable internal energy receiver for receiving wireless energy. The energy receiver preferably has an internal first coil and a first electronic circuit connected to the first coil. The system further comprises an external energy transmitter for transmitting wireless energy, that preferably has an external second coil and a second electronic circuit connected to the second coil, wherein the external second coil of the energy transmitter transmits wireless energy which is received by the first coil of the energy receiver. Such a system can further comprise a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. Alternatively, in such a system the feedback device can be adapted to communicate out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factors between the first and second coils. The energy transmitter preferably regulates the transmitted energy in response to the obtained coupling factor. In one embodiment, the external second coil is adapted to be moved in relation to the internal first coil to establish the optimal placement of the second coil, in which the coupling factor is maximized. In another embodiment, the external second coil is adapted to calibrate the amount of transferred energy to achieve the feedback information in the determination device, before the coupling factor is maximized.

EXEMPLIFYING DESCRIPTION OF THE INVENTION

The present invention will now be described in more detail by way of non-limiting examples and with reference to the accompanying drawings, wherein:

FIG. 1 is a schematic picture of patient having the inventive apparatus implanted.

FIG. 2a is a schematic picture of an embodiment of the apparatus as implanted.

FIG. 2b is a section of the apparatus FIG. 2a illustrating the detachable coupling between parts of the apparatus.

FIG. 3 is an illustration of the apparatus of FIG. 2a in its operating mode of discharging urine from the urinary bladder through the urethra.

FIG. 4 is an illustration of the apparatus FIG. 2a when the urine bladder is refilled with urine, also showing a special embodiment where the bladder operating reservoir is hydraulically connected to the ureter restriction devices.

FIG. 6 illustrates a system according to the invention, wherein the system schematically includes an apparatus of the invention implanted in a patient.

FIGS. 7-21 schematically show various embodiments of the system for wirelessly powering the apparatus shown in FIG. 1.

FIG. 22 is a schematic block diagram illustrating an arrangement for supplying an accurate amount of energy used for the operation of the apparatus shown in FIG. 6.

Figure 23:
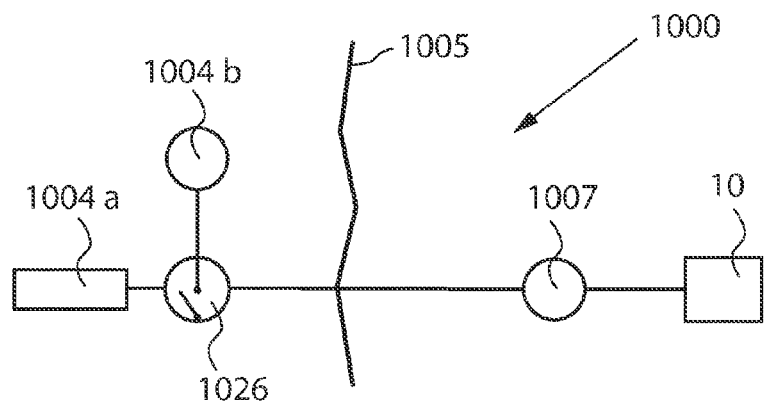

FIG. 23 schematically shows an embodiment of the system, in which the apparatus is operated with wire bound energy.

Figure 24:
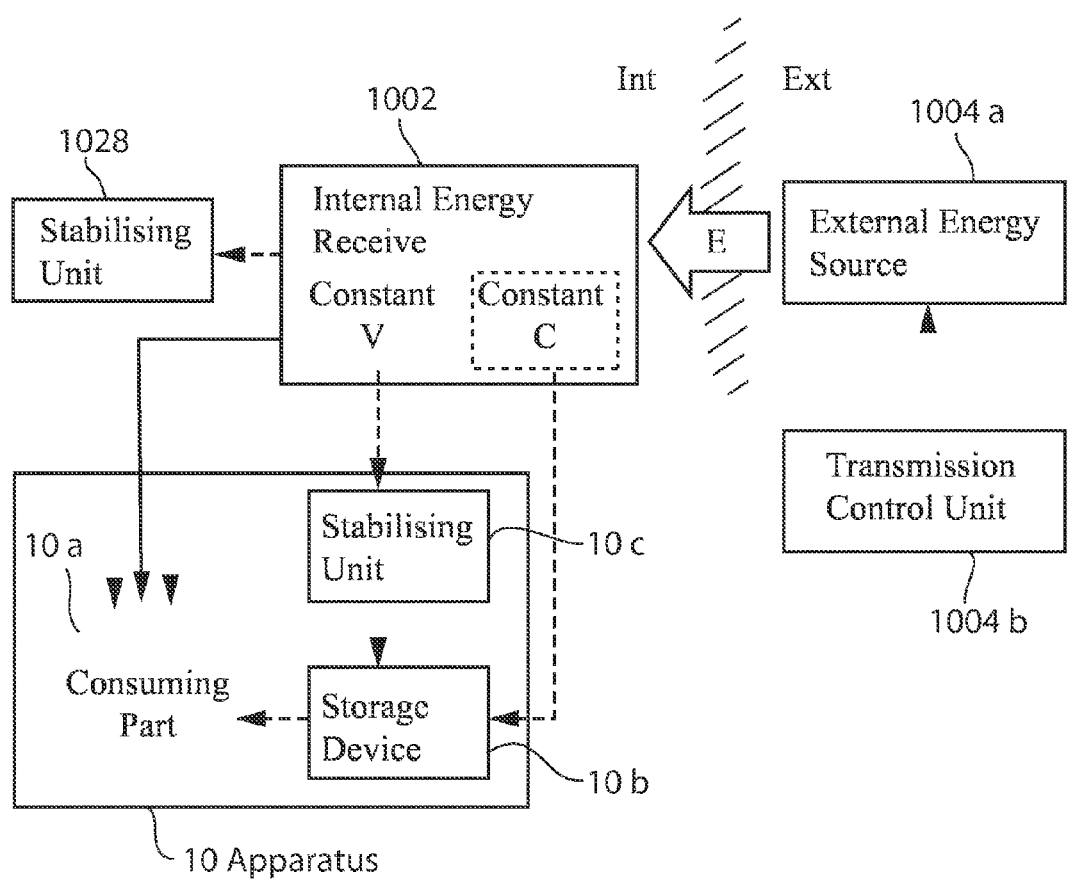

FIG. 24 is a more detailed block diagram of an arrangement for controlling the transmission of wireless energy used for the operation of the apparatus shown in FIG. 6.

Figure 19:
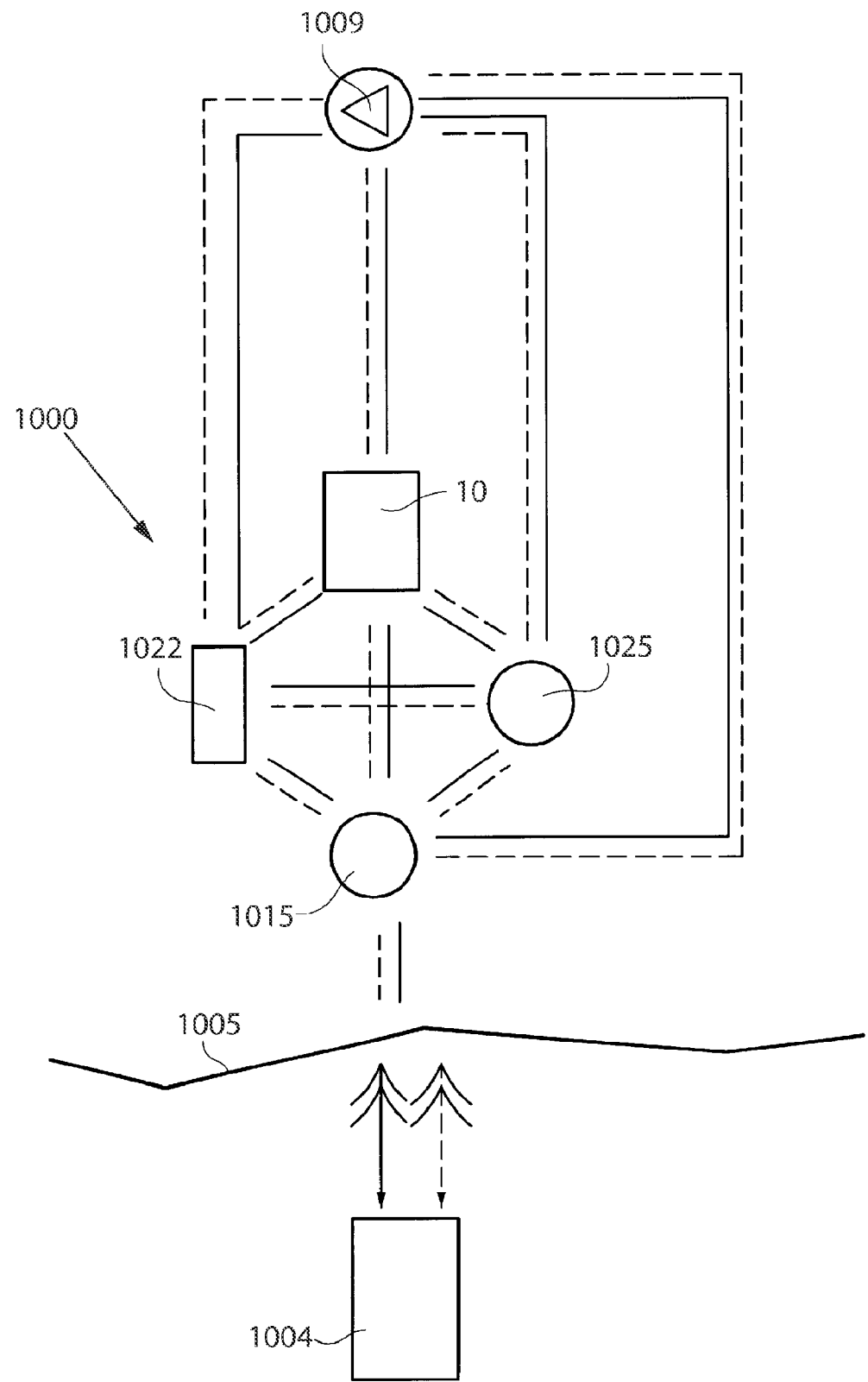
Figure 25:
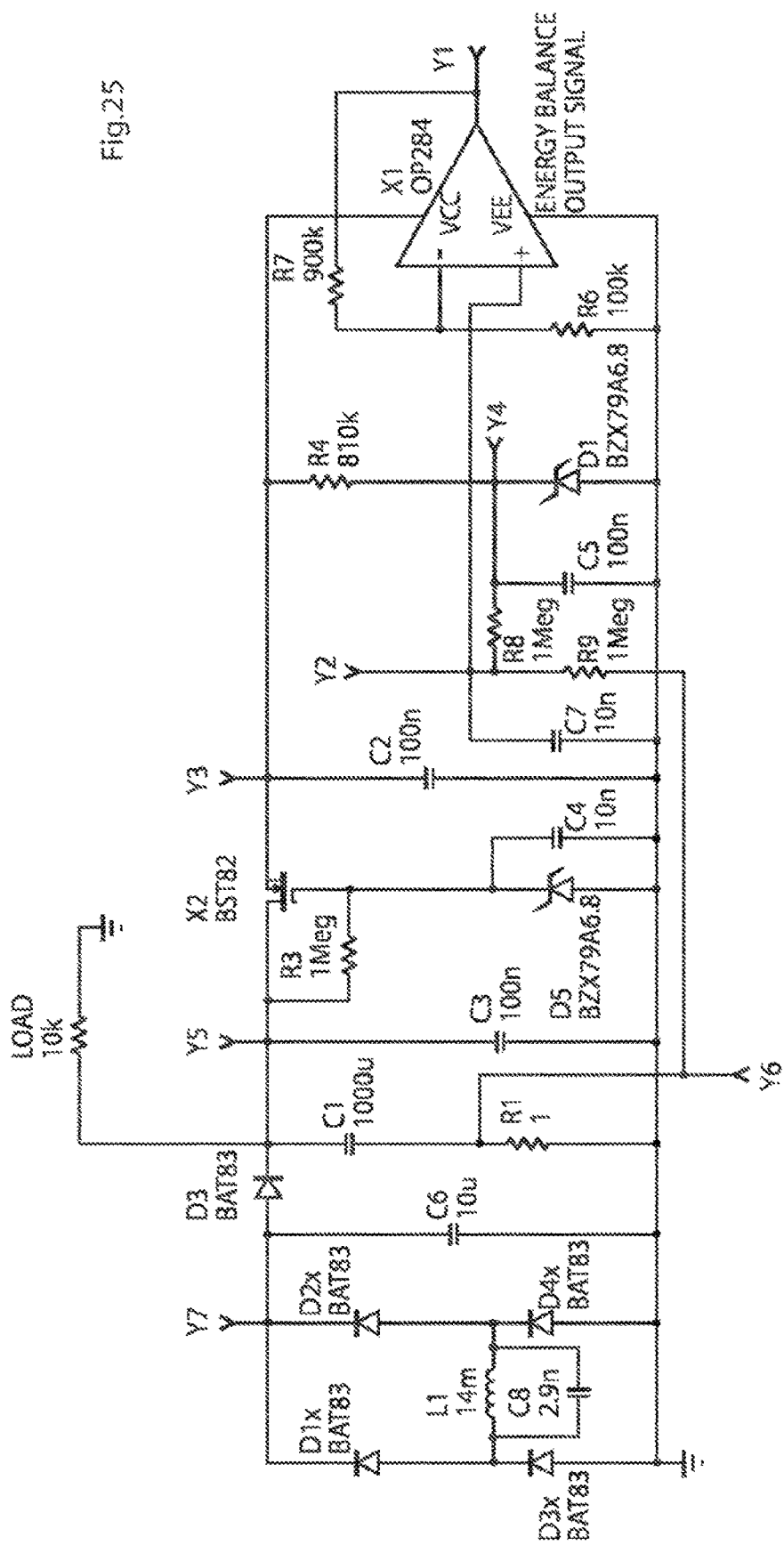

FIG. 25 is a circuit for the arrangement shown in FIG. 19, according to a possible implementation example.

FIGS. 26-32 show various ways of arranging hydraulic or pneumatic powering of an apparatus implanted in a patient.

By reference to FIG. 1 and FIG. 2a the apparatus has an expandable member 20 with a cavity for accommodating hydraulic fluid that is placed inside the urinary bladder 30 which contains urine arrived from the ureters 32A, 32B. A control device 50 operates the expansion and thereby the volume of the expandable member. The control device 50 has a control assembly 52 connected to a bladder operating reservoir 54 for hydraulic fluid which is connected to the expandable member with an interconnecting device 56 for transporting hydraulic fluid between the bladder operating reservoir 54 and the expandable member 20. A pump 53 is supporting the fluid transportation. The interconnecting device 56 is a tube-shaped device surgically incised through the wall of the urinary bladder and attached thereto with tunneling technique whereby the bladder wall is sutured to itself The interconnecting device is supported by the net 58 which seals fixates by admitting tissue in-growth. In FIG. 2a the interconnecting device 56 is attached to a detachable coupling 55 that attaches the bladder operating reservoir with the expandable member as will be described below with FIG. 2b. The control assembly 52 is located in the patient and includes a number of functional elements necessary for operating the apparatus, such as an operating pump 529 for the hydraulic fluid, a source of energy 521 for driving the operating pump and other energy consuming parts of the apparatus. An external energizer 60 transfers wireless energy to an energy transforming device 522 so the source of energy 521 can be supplemented. An external control unit 70 provides wireless communication with an internal control unit 523 for operating the apparatus. Also, the pressure sensor 57 is connected to a sensor control function 524 of the control assembly. The control assembly 52 has an internal part 52A including the mentioned functions and an external part 52B which includes an injection port 521B and a manually operable switch 522B. One or more parts of the control device may be implanted subcutaneously or in the abdominal cavity or the pelvic region or any other suitable place inside the body. The embodiment depicted in FIG. 2a is adapted for a patient suffering from a complication where the urinary sphincter is permanently closed. For this reason, the expandable member 20 of the apparatus needs to exert a considerable pressure (about 60-80 cm water pressure) to force urine out from the bladder and urine may thereby backflow through ureters 32A, 32B with potential risks for damaging the kidneys. To prevent from any such complications, the control device is provided with restriction devices 59A, 59B arranged to temporarily contract the ureters and close them during the operation of discharging urine with the expandable member. The restriction devices are operated from the control assembly in manner to perform their temporary contraction during the discharge performance. Suitable mechanical or hydraulically operated restriction devices and their control are described in more detail in European Patents Nos. EP 1253880; EP 1284691; and EP 1263355. The urine pressure in the ureter is normally around 50 cm water, however short term pressure increase is most likely not damaging the kidneys and therefore the restriction devices 59A and 59B may be omitted.

When the pump 53 is not pumping to fill the expandable member and if the passage-way 56 between the bladder operating reservoir and the expandable member is free, then the expandable member is emptied by urine filling the bladder. Another alternative is that the pump 53 starts in steps to empty the expandable member for example pressure controlled or controlled by any other input sensor as mentioned elsewhere. A second connection 56B is introduced between the expandable member 20 and the bladder operating reservoir 54. The second connection is adapted to admit transportation of fluid from the member 20 to the bladder operating reservoir when the connection is closed. If the pumping volume capacity is significantly much larger than the emptying capacity of the second connection this connection may always stand open, also when the pump 53 transports fluid from the bladder operating reservoir 54 to the member 20. Introduction of the second connection shall be regarded as an optional alternative of the apparatus.

FIG. 2b is closer view of the detachable coupling 55 in FIG. 2a and its two mating parts 55A and 55B. A first mating part 55A is a part of the control device 50 and is connected to the bladder operating reservoir 54. The second mating part 55B is arranged on the expandable member 20. The two mating parts are readily attachable and detachable in order to conveniently attach or detach the expandable member to the control device 50. Accordingly, the expandable member becomes readily replaceable by intervention through the urethra with a suitable instrument. For this purpose the expandable member is capable of assuming an essentially cylindrical elongated shape to conveniently pass through the urethra. FIG. 2b also shows the second connection 56B as a part of the detachable coupling.

By reference to FIG. 2a and FIG. 3, the apparatus in operated by activating the operating pump of the control assembly 54 which is operable in response from a signal from a remote control 70. The control assembly can also be connected to a pressure sensor 57 for monitoring the urinary pressure of the bladder. Several different types of input sensors may be used determining for example stretching or bending or pressure in the urine bladder wall or for example sensing volume or pressure inside the urine bladder. Most likely these sensors is only indirectly causing the bladder to be emptied by presenting an alarm for the patient informing that it is time to empty the bladder. Such an alarm is generated audible or visually. The remote control 70 may control a subcutaneous switch 525 for controlling the emptying of the bladder or communicating via the body used as a wire or with wireless communication. The pump now transports hydraulic fluid from the bladder operating reservoir 54, through the interconnection device 56 to the cavity of the expandable member 20, which thereby increases in volume in the urinary bladder and discharges urine through the urethra at a pressure that overcomes the closing force of the urethral sphincter, so voiding of the urinary bladder is accomplished. During this operation the control assembly operates to close restriction device 59A, 59B to prevent any urinary backflow in the ureters. When the discharging performance is finished and the operating pump is inactive, the restriction devices 59A, 59B are released so urine can refill the urinary bladder. By the pressure of the refilled urine, the expandable member 20 subsequently collapses to retain a shape as shown in FIG. 2 when ready for a new performance as monitored by the pressure sensor.

Some patients having urinary retention also have urinary incontinence. In such a case a separate urinary sphincter is included in the system, a restriction device closing the urethra until the patient wants to urinate. In such a case lower pressure is needed to empty the bladder because the no force would be needed to open the sphincter by intra bladder pressure. In this case the restriction devices 59A and 59B may be omitted.

Figure 5:
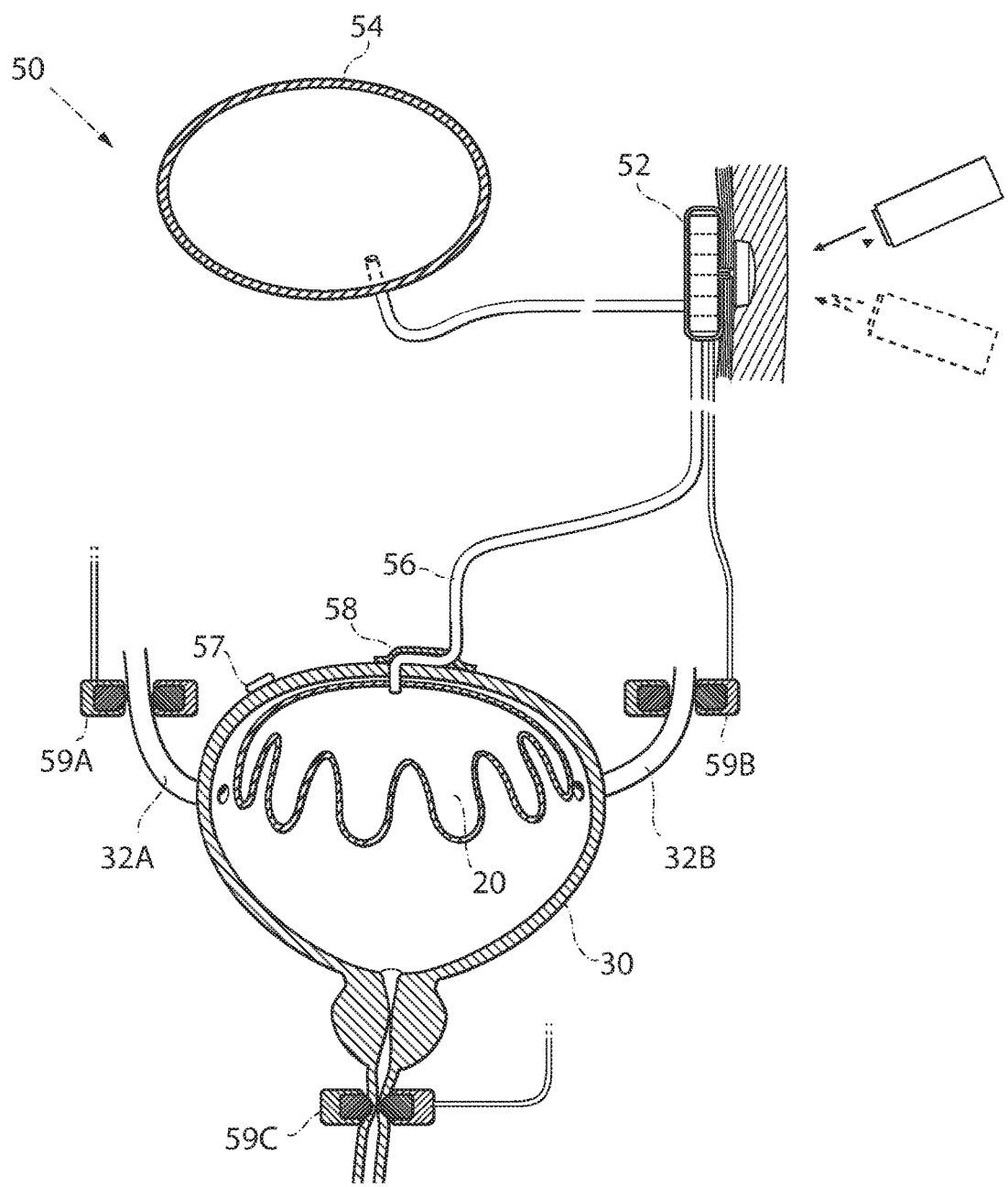
FIG. 5 illustrates another embodiment of the apparatus.

The bladder operating reservoir 54 may be placed anywhere inside the body, however preferable in the abdominal cavity, maybe placed onto the urine bladder or in the pelvic region. The amount of liquid in the bladder operating reservoir may be calibrated with fluid by using the injection port 521B and a subcutaneous reservoir 526 placed inside the body within reach from a special injection port needle. The subcutaneous reservoir may also be omitted and only the injection port may be used to fill and empty the expandable member. With the described embodiment it is also conceivable to control the duration/force of the urine discharge process, e.g. that data from the pressure sensor measuring the urinary pressure or easier the pressure inside the expandable member in the bladder controls the operation pump by logic in the control assembly. It should be noted that the expandable member may be elastic or only flexible, within the used pressure inside the same. FIG. 3 shows the apparatus of FIG. 2 (without the control device 50) when discharging urine. The restriction devices 59A, 59B now close the ureters 32A, 32B while urinary sphincter 59C is open. FIG. 4 shows the apparatus of FIG. 3 when the urinary bladder is being refilled with urine and hydraulic fluid is returned to the bladder operating reservoir 54. The restriction devices 59A, 59B are now open while urinary sphincter 59C is closed. FIG. 4 also shows an embodiment wherein the restriction devices for ureters are hydraulically operated with hydraulic fluid from a special section of the bladder operating reservoir. The hydraulic fluid for operating the restriction devices can be displaced from the reservoir when the remaining section of the reservoir is filled as a consequence of the urinary pressure exerted on the expandable member. FIG. 5 illustrates another embodiment of the apparatus of FIG. 2*a*. Here the bladder operating reservoir 54 is hydraulically connected to a pump 527 in the control assembly 52 which operates to pump hydraulic fluid to the expandable member 20.

It should be understood that the described embodiment can be modified within the scope of the appended claims.

FIG. 6 illustrates a system for treating urinary incontinence with an apparatus 10 of the present invention and generally described or as illustrated FIGS. 1 to 5. The system is placed in the abdomen of a patient. An implanted energy-transforming device 302 is adapted to supply energy consuming components of the apparatus with energy via a power supply line 303. An external energy-transmission device 304 for non-invasively energizing the apparatus 10 transmits energy by at least one wireless energy signal. The implanted energy-transforming device 1002 transforms energy from the wireless energy signal into electric energy which is supplied via the power supply line 1003.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 1004 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 1002 is provided for transforming wireless energy of a first form transmitted by the energy-transmission device 1004 into energy of a second form, which typically is different from the energy of the first form. The implanted apparatus 10 is operable in response to the energy of the second form. The energy-transforming device 1002 may directly power the apparatus with the second form energy, as the energy-transforming device 1002 transforms the first form energy transmitted by the energy-transmission device 1004 into the second form energy. The system may further include an implantable accumulator, wherein the second form energy is used at least partly to charge the accumulator.

Alternatively, the wireless energy transmitted by the energy-transmission device 1004 may be used to directly power the apparatus, as the wireless energy is being transmitted by the energy-transmission device 1004. Where the system comprises an operation device for operating the apparatus, as will be described below, the wireless energy transmitted by the energy-transmission device 1004 may be used to directly power the operation device to create kinetic energy for the operation of the apparatus.

The wireless energy of the first form may comprise sound waves and the energy-transforming device 1002 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus.

The external energy-transmission device 1004 also includes a wireless remote control having an external signal transmitter for transmitting a wireless control signal for non-invasively controlling the apparatus. The control signal is received by an implanted signal receiver which may be incorporated in the implanted energy-transforming device 1002 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

FIG. 7 illustrates the system of FIG. 6 in the form of a more generalized block diagram showing the apparatus 10, the energy-transforming device 1002 powering the apparatus 10 via power supply line 1003, and the external energy-transmission device 1004, The patient's skin 1005, generally shown by a vertical line, separates the interior of the patient to the right of the line from the exterior to the left of the line.

FIG. 8 shows an embodiment of the invention identical to that of FIG. 7, except that a reversing device in the form of an electric switch 1006 operable for example by polarized energy also is implanted in the patient for reversing the apparatus 10. When the switch is operated by polarized energy the wireless remote control of the external energy-transmission device 1004 transmits a wireless signal that carries polarized energy and the implanted energy-transforming device 1002 transforms the wireless polarized energy into a polarized current for operating the electric switch 1006. When the polarity of the current is shifted by the implanted energy-transforming device 1002 the electric switch 1006 reverses the function performed by the apparatus 10.

FIG. 9 shows an embodiment of the invention identical to that of FIG. 7, except that an operation device 1007 implanted in the patient for operating the apparatus 10 is provided between the implanted energy-transforming device 1002 and the apparatus 10. This operation device can be in the form of a motor 1007, such as an electric servomotor. The motor 1007 is powered with energy from the implanted energy-transforming device 1002, as the remote control of the external energy-transmission device 1004 transmits a wireless signal to the receiver of the implanted energy-transforming device 1002.

FIG. 10 shows an embodiment of the invention identical to that of FIG. 7, except that it also comprises an operation device is in the form of an assembly 1008 including a motor/pump unit 1009 and a fluid reservoir 1010 is implanted in the patient. In this case the apparatus 10 is hydraulically operated, i.e. hydraulic fluid is pumped by the motor/pump unit 1009 from the fluid reservoir 1010 through a conduit 1011 to the apparatus 10 to operate the apparatus, and hydraulic fluid is pumped by the motor/pump unit 1009 back from the apparatus 10 to the fluid reservoir 1010 to return the apparatus to a starting position. The implanted energy-transforming device 1002 transforms wireless energy into a current, for example a polarized current, for powering the motor/pump unit 1009 via an electric power supply line 1012.

Instead of a hydraulically operated apparatus 10, it is also envisaged that the operation device comprises a pneumatic operation device. In this case, the hydraulic fluid can be pressurized air to be used for regulation and the fluid reservoir is replaced by an air chamber.

In all of these embodiments the energy-transforming device 1002 may include a rechargeable accumulator like a battery or a capacitor to be charged by the wireless energy and supplies energy for any energy consuming part of the system.

As an alternative, the wireless remote control described above may be replaced by manual control of any implanted part to make contact with by the patient's hand most likely indirect, for example a press button placed under the skin.

Figure 11:
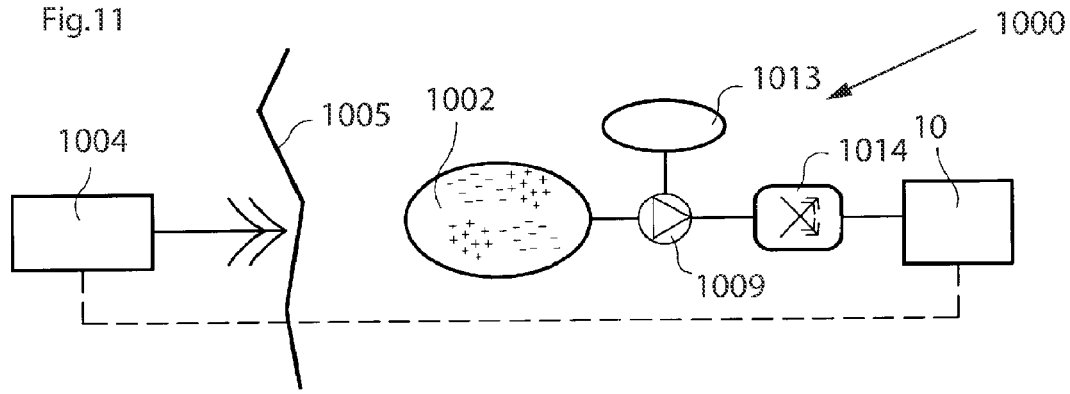

FIG. 11 shows an embodiment of the invention comprising the external energy-transmission device 1004 with its wireless remote control, the apparatus 10, in this case hydraulically operated, and the implanted energy-transforming device 1002, and further comprising a hydraulic fluid reservoir 1013, a motor/pump unit 1009 and an reversing device in the form of a hydraulic valve shifting device 1014, all implanted in the patient. Of course the hydraulic operation could easily be performed by just changing the pumping direction and the hydraulic valve may therefore be omitted. The remote control may be a device separated from the external energy-transmission device or included in the same. The motor of the motor/pump unit 1009 is an electric motor. In response to a control signal from the wireless remote control of the external energy-transmission device 1004, the implanted energy-transforming device 1002 powers the motor/pump unit 1009 with energy from the energy carried by the control signal, whereby the motor/pump unit 1009 distributes hydraulic fluid between the hydraulic fluid reservoir 1013 and the apparatus 10. The remote control of the external energy-transmission device 1004 controls the hydraulic valve shifting device 1014 to shift the hydraulic fluid flow direction between one direction in which the fluid is pumped by the motor/pump unit 1009 from the hydraulic fluid reservoir 1013 to the apparatus 10 to operate the apparatus, and another opposite direction in which the fluid is pumped by the motor/pump unit 1009 back from the apparatus 10 to the hydraulic fluid reservoir 1013 to return the apparatus to a starting position.

FIG. 7 shows an embodiment of the invention comprising the external energy-transmission device 1004 with its wireless remote control, the apparatus 10, the implanted energy-transforming device 1002, an implanted internal control unit 1015 controlled by the wireless remote control of the external energy-transmission device 1004, an implanted accumulator 1016 and an implanted capacitor 1017. The internal control unit 1015 arranges storage of electric energy received from the implanted energy-transforming device 1002 in the accumulator 1016, which supplies energy to the apparatus 10. In response to a control signal from the wireless remote control of the external energy-transmission device 1004, the internal control unit 1015 either releases electric energy from the accumulator 1016 and transfers the released energy via power lines 1018 and 1019, or directly transfers electric energy from the implanted energy-transforming device 1002 via a power line 1020, the capacitor 1017, which stabilizes the electric current, a power line 1021 and the power line 1019, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

Figure 12:
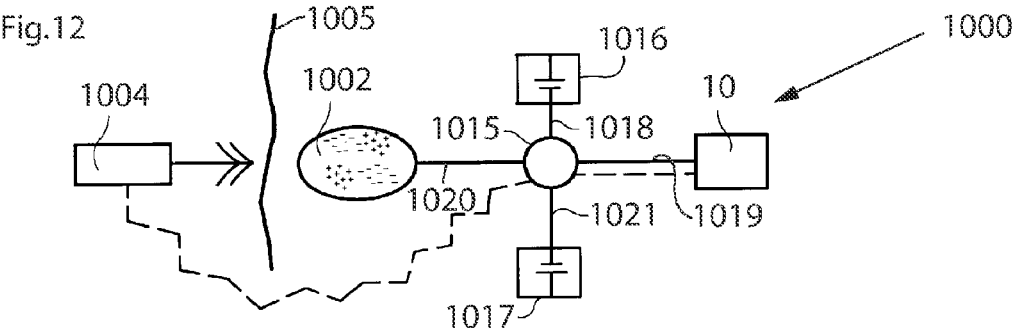

In accordance with an alternative, the capacitor 1017 in the embodiment of FIG. 12 may be omitted. In accordance with another alternative, the accumulator 1016 in this embodiment may be omitted.

Figure 13:
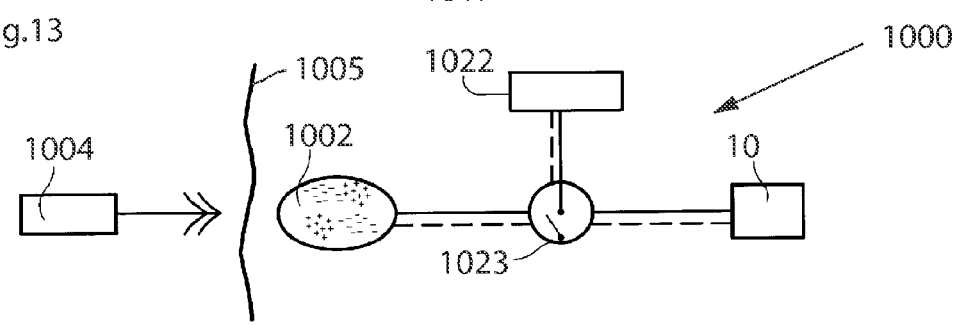

FIG. 13 shows an embodiment of the invention identical to that of FIG. 7, except that a battery 1022 for supplying energy for the operation of the apparatus 10 and an electric switch 1023 for switching the operation of the apparatus 10 also are implanted in the patient. The electric switch 1023 may be controlled by the remote control and may also be operated by the energy supplied by the implanted energy-transforming device 1002 to switch from an off mode, in which the battery 1022 is not in use, to an on mode, in which the battery 1022 supplies energy for the operation of the apparatus 10.

Figure 14:
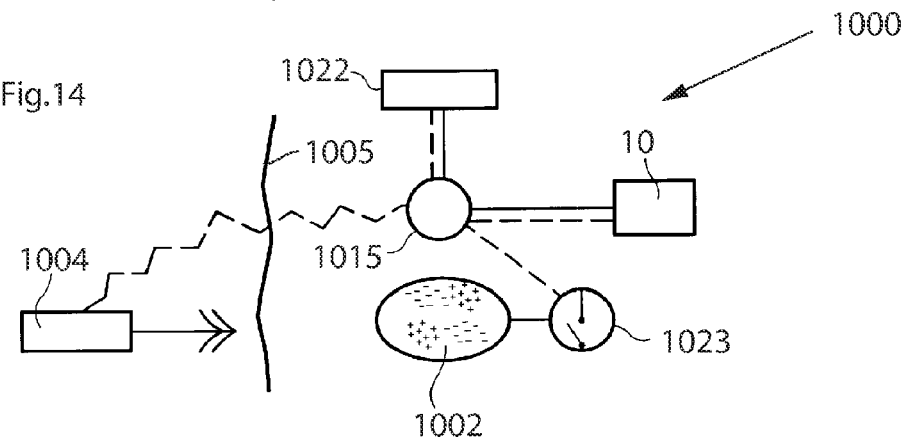

FIG. 14 shows an embodiment of the invention identical to that of FIG. 13, except that an internal control unit 1015 controllable by the wireless remote control of the external energy-transmission device 1004 also is implanted in the patient. In this case, the electric switch 1023 is operated by the energy supplied by the implanted energy-transforming device 1002 to switch from an off mode, in which the wireless remote control is prevented from controlling the internal control unit 1015 and the battery is not in use, to a standby mode, in which the remote control is permitted to control the internal control unit 1015 to release electric energy from the battery 1022 for the operation of the apparatus 10.

Figure 15:
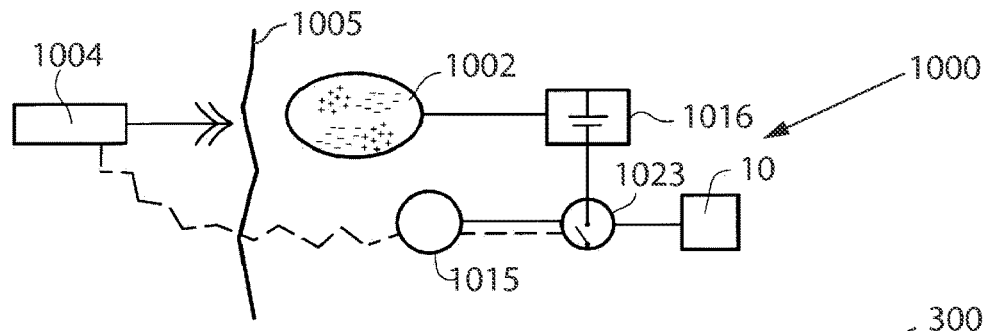

FIG. 15 shows an embodiment of the invention identical to that of FIG. 14, except that an accumulator 1016 is substituted for the battery 1022 and the implanted components are interconnected differently. In this case, the accumulator 1016 stores energy from the implanted energy-transforming device 1002. In response to a control signal from the wireless remote control of the external energy-transmission device 1004, the internal control unit 1015 controls the electric switch 1023 to switch from an off mode, in which the accumulator 1016 is not in use, to an on mode, in which the accumulator 1016 supplies energy for the operation of the apparatus 10. The accumulator may be combined with or replaced by a capacitor.

Figure 16:
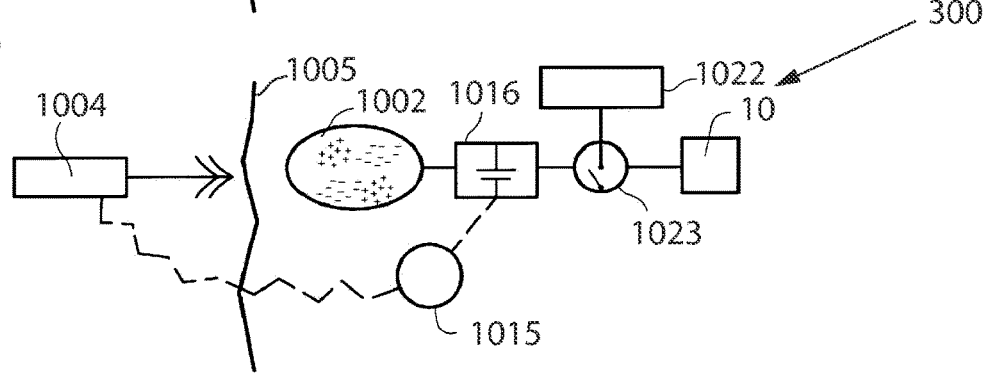

FIG. 16 shows an embodiment of the invention identical to that of FIG. 15, except that a battery 1022 also is implanted in the patient and the implanted components are interconnected differently. In response to a control signal from the wireless remote control of the external energy-transmission device 1004, the internal control unit 1015 controls the accumulator 1016 to deliver energy for operating the electric switch 1023 to switch from an off mode, in which the battery 1022 is not in use, to an on mode, in which the battery 1022 supplies electric energy for the operation of the apparatus 10.

Alternatively, the electric switch 1023 may be operated by energy supplied by the accumulator 1016 to switch from an off mode, in which the wireless remote control is prevented from controlling the battery 1022 to supply electric energy and is not in use, to a standby mode, in which the wireless remote control is permitted to control the battery 1022 to supply electric energy for the operation of the apparatus 10.

It should be understood that the switch 1023 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 17:
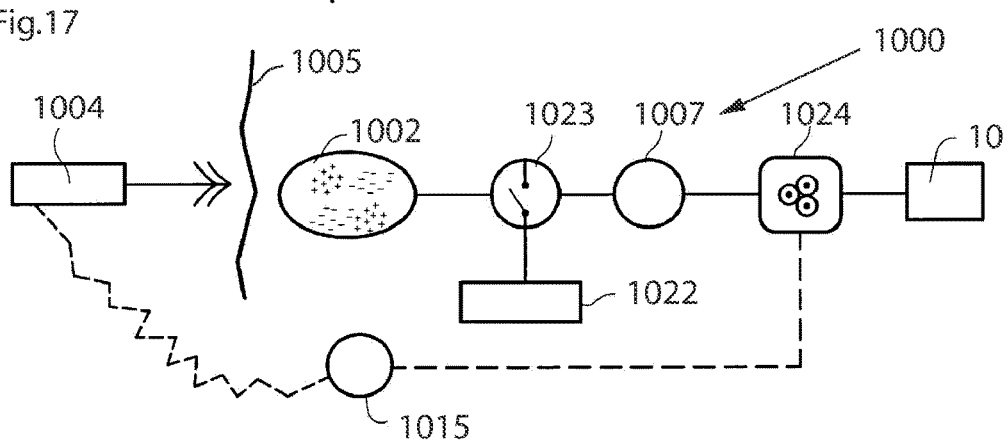

FIG. 17 shows an embodiment of the invention identical to that of FIG. 13, except that a motor 1007, a mechanical reversing device in the form of a gear box 1024, and an internal control unit 1015 for controlling the gear box 1024 also are implanted in the patient. The internal control unit 1015 controls the gear box 1024 to reverse the function performed by the apparatus 10 (mechanically operated). Even simpler is to switch the direction of the motor electronically. The gear box interpreted in its broadest embodiment may stand for a servo arrangement saving force for the operation device in favour of longer stroke to act.

Figure 18:
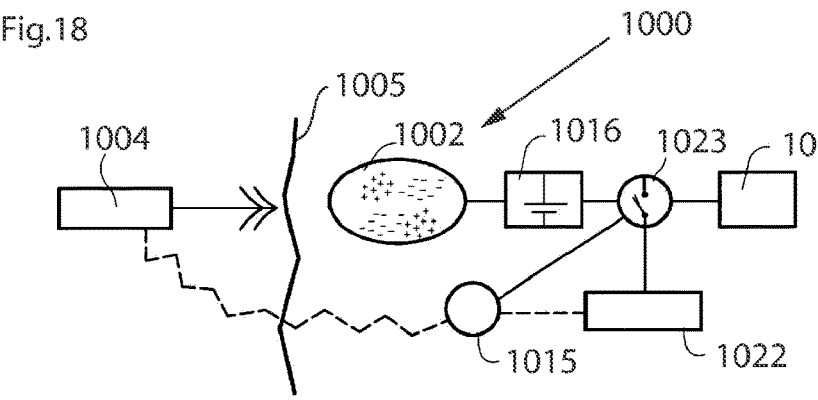

FIG. 18 shows an embodiment of the invention identical to that of FIG. 24 except that the implanted components are interconnected differently. Thus, in this case the internal control unit 1015 is powered by the battery 1022 when the accumulator 1016, suitably a capacitor, activates the electric switch 1023 to switch to an on mode. When the electric switch 1023 is in its on mode the internal control unit 1015 is permitted to control the battery 1022 to supply, or not supply, energy for the operation of the apparatus 10.

FIG. 19 schematically shows conceivable combinations of implanted components of the apparatus for achieving various communication options. Basically, there are the apparatus 10, the internal control unit 1015, motor or pump unit 1009, and the external energy-transmission device 1004 including the external wireless remote control. As already described above the wireless remote control transmits a control signal which is received by the internal control unit 1015, which in turn controls the various implanted components of the apparatus.

A feedback device, preferably comprising a sensor or measuring device 1025, may be implanted in the patient for sensing a physical parameter of the patient. The physical parameter may be at least one selected from the group consisting of pressure, volume, diameter, stretching, elongation, extension, movement, bending, elasticity, muscle contraction, nerve impulse, body temperature, blood pressure, blood flow, heartbeats and breathing. The sensor may sense any of the above physical parameters. For example, the sensor may be a pressure or motility sensor. Alternatively, the sensor 1025 may be arranged to sense a functional parameter. The functional parameter may be correlated to the transfer of energy for charging an implanted energy source and may further include at least one selected from the group of parameters consisting of; electricity, any electrical parameter, pressure, volume, diameter, stretch, elongation, extension, movement, bending, elasticity, temperature and flow.

The feedback may be sent to the internal control unit or out to an external control unit preferably via the internal control unit. Feedback may be sent out from the body via the energy transfer system or a separate communication system with receiver and transmitters.

The internal control unit 1015, or alternatively the external wireless remote control of the external energy-transmission device 1004, may control the apparatus 10 in response to signals from the sensor 1025. A transceiver may be combined with the sensor 1025 for sending information on the sensed physical parameter to the external wireless remote control. The wireless remote control may comprise a signal transmitter or transceiver and the internal control unit 1015 may comprise a signal receiver or transceiver. Alternatively, the wireless remote control may comprise a signal receiver or transceiver and the internal control unit 1015 may comprise a signal transmitter or transceiver. The above transceivers, transmitters and receivers may be used for sending information or data related to the apparatus 10 from inside the patient's body to the outside thereof.

Where the motor/pump unit 1009 and battery 1022 for powering the motor/pump unit 1009 are implanted, information related to the charging of the battery 1022 may be fed back. To be more precise, when charging a battery or accumulator with energy feed back information related to said charging process is sent and the energy supply is changed accordingly.

FIG. 20 shows an alternative embodiment wherein the apparatus 10 is regulated from outside the patient's body. The system 1000 comprises a battery 1022 connected to the apparatus 10 via a subcutaneous electric switch 1026. Thus, the regulation of the apparatus 10 is performed non-invasively by manually pressing the subcutaneous switch, whereby the operation of the apparatus 10 is switched on and off. It will be appreciated that the shown embodiment is a simplification and that additional components, such as an internal control unit or any other part disclosed in the present application can be added to the system. Two subcutaneous switches may also be used. In the preferred embodiment one implanted switch sends information to the internal control unit to perform a certain predetermined performance and when the patient press the switch again the performance is reversed.

FIG. 21 shows an alternative embodiment, wherein the system 1000 comprises a hydraulic fluid reservoir 1013 hydraulically connected to the apparatus. Non-invasive regulation is performed by manually pressing the hydraulic reservoir connected to the apparatus.

The system may include an external data communicator and an implantable internal data communicator communicating with the external data communicator. The internal communicator feeds data related to the apparatus or the patient to the external data communicator and/or the external data communicator feeds data to the internal data communicator.

FIG. 22 schematically illustrates an arrangement of the system that is capable of sending information from inside the patient's body to the outside thereof to give feedback information related to at least one functional parameter of the apparatus or system, or related to a physical parameter of the patient, in order to supply an accurate amount of energy to an implanted internal energy receiver 1002 connected to implanted energy consuming components of the apparatus 10. Such an energy receiver 1002 may include an energy source and/or an energy-transforming device. Briefly described, wireless energy is transmitted from an external energy source 1004a located outside the patient and is received by the internal energy receiver 1002 located inside the patient. The internal energy receiver is adapted to directly or indirectly supply received energy to the energy consuming components of the apparatus 10 via a switch 1026. An energy balance is determined between the energy received by the internal energy receiver 1002 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIG. 23 the patient's skin is indicated by a vertical line 1005. Here, the energy receiver comprises an energy-transforming device 1002 located inside the patient, preferably just beneath the patient's skin 1005. Generally speaking, the implanted energy-transforming device 1002 may be placed in the abdomen, thorax, muscle fascia (e.g. in the abdominal wall), subcutaneously, or at any other suitable location. The implanted energy-transforming device 1002 is adapted to receive wireless energy E transmitted from the external energy-source 1004a provided in an external energy-transmission device 1004 located outside the patient's skin 1005 in the vicinity of the implanted energy-transforming device 1002.

As is well known in the art, the wireless energy E may generally be transferred by means of any suitable Transcutaneous Energy Transfer (TET) device, such as a device including a primary coil arranged in the external energy source 1004a and an adjacent secondary coil arranged in the implanted energy-transforming device 1002. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor. However, the present invention is generally not limited to any particular energy transfer technique, TET devices or energy sources, and any kind of wireless energy may be used.

The amount of energy received by the implanted energy receiver may be compared with the energy used by the implanted components of the apparatus. The term "energy used" is then understood to include also energy stored by implanted components of the apparatus. A control device includes an external control unit 1004b that controls the external energy source 1004a based on the determined energy balance to regulate the amount of transferred energy. In order to transfer the correct amount of energy, the energy balance and the required amount of energy is determined by means of a determination device including an implanted internal control unit 1015 connected between the switch 1026 and the apparatus 10. The internal control unit 1015 may thus be arranged to receive various measurements obtained by suitable sensors or the like, not shown, measuring certain characteristics of the apparatus 10, somehow reflecting the required amount of energy needed for proper operation of the apparatus 10. Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 1016 may optionally be connected to the implanted energy-transforming device 1002 via the control unit 1015 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 1002, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 1015. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 1015 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 1015 is further connected to an internal signal transmitter 1027, arranged to transmit a control signal reflecting the determined required amount of energy, to an external signal receiver 1004c connected to the external control unit 1004b. The amount of energy transmitted from the external energy source 1004a may then be regulated in response to the received control signal.

Alternatively, the determination device may include the external control unit 1004b. In this alternative, sensor measurements can be transmitted directly to the external control unit 1004b wherein the energy balance and/or the currently required amount of energy can be determined by the external control unit 1004b, thus integrating the above-described function of the internal control unit 1015 in the external control unit 1004b. In that case, the internal control unit 1015 can be omitted and the sensor measurements are supplied directly to the internal signal transmitter 1027 which sends the measurements over to the external signal receiver 1004c and the external control unit 1004b. The energy balance and the currently required amount of energy can then be determined by the external control unit 1004*b* based on those sensor measurements.

Hence, the present solution according to the arrangement of FIG. 22 employs the feed back of information indicating the required energy, which is more efficient than previous solutions because it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

The internal signal transmitter 1027 and the external signal receiver 1004*c* may be implemented as separate units using suitable signal transfer means, such as radio, IR (Infrared) or ultrasonic signals. Alternatively, the internal signal transmitter 1027 and the external signal receiver 1004*c* may be integrated in the implanted energy-transforming device 1002 and the external energy source 1004*a*, respectively, so as to convey control signals in a reverse direction relative to the energy transfer, basically using the same transmission technique. The control signals may be modulated with respect to frequency phase or amplitude.

Thus, the feedback information may be transferred either by a separate communication system including receivers and transmitters or may be integrated in the energy system. In accordance with the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this system in the arrangement of FIG. 17, the switch 1026 is either separate and controlled by the internal control unit 1015, or integrated in the internal control unit 1015. It should be understood that the switch 1026 should be interpreted in its broadest embodiment. This means a transistor, MCU, MCPU, ASIC FPGA or a DA converter or any other electronic component or circuit that may switch the power on and off.

To conclude, the energy supply arrangement illustrated in FIG. 22 may operate basically in the following manner. The energy balance is first determined by the internal control unit 1015 of the determination device. A control signal reflecting the required amount of energy is also created by the internal control unit 1015, and the control signal is transmitted from the internal signal transmitter 1027 to the external signal receiver 1004*c*. Alternatively, the energy balance can be determined by the external control unit 1004*b* instead depending on the implementation, as mentioned above. In that case, the control signal may carry measurement results from various sensors. The amount of energy emitted from the external energy source 1004*a* can then be regulated by the external control unit 1004*b*, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 1004*a*, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil. The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

With reference to FIG. 23, although wireless transfer of energy for operating the apparatus has been described above to enable non-invasive operation, it will be appreciated that the apparatus can be operated with wire bound energy as well. Such an example is shown in FIG. 18, wherein an external switch 1026 is interconnected between the external energy source 1004*a* and an operation device, such as an electric motor 1007 operating the apparatus 10. An external control unit 1004*b* controls the operation of the external switch 1026 to effect proper operation of the apparatus 10.

FIG. 24 illustrates different embodiments for how received energy can be supplied to and used by the apparatus 10. Similar to the example of FIG. 17, an internal energy receiver 1002 receives wireless energy E from an external energy source 1004*a* which is controlled by a transmission control unit 1004*b*. The internal energy receiver 1002 may comprise a constant voltage circuit, indicated as a dashed box "constant V" in the figure, for supplying energy at constant voltage to the apparatus 10. The internal energy receiver 1002 may further comprise a constant current circuit, indicated as a dashed box "constant C" in the figure, for supplying energy at constant current to the apparatus 10.

The apparatus 10 comprises an energy consuming part 10*a*, which may be a motor, pump, restriction device, or any other medical appliance that requires energy for its electrical operation. The apparatus 10 may further comprise an energy storage device 10*b* for storing energy supplied from the internal energy receiver 1002. Thus, the supplied energy may be directly consumed by the energy consuming part 10*a*, or stored by the energy storage device 10*b*, or the supplied energy may be partly consumed and partly stored. The apparatus 10 may further comprise an energy stabilizing unit 10*c* for stabilizing the energy supplied from the internal energy receiver 1002. Thus, the energy may be supplied in a fluctuating manner such that it may be necessary to stabilize the energy before consumed or stored.

The energy supplied from the internal energy receiver 1002 may further be accumulated and/or stabilized by a separate energy stabilizing unit 1028 located outside the apparatus 10, before being consumed and/or stored by the apparatus 10. Alternatively, the energy stabilizing unit 1028 may be integrated in the internal energy receiver 1002. In either case, the energy stabilizing unit 1028 may comprise a constant voltage circuit and/or a constant current circuit.

It should be noted that FIG. 22 and FIG. 24 illustrate some possible but non-limiting implementation options regarding how the various shown functional components and elements can be arranged and connected to each other. However, the skilled person will readily appreciate that many variations and modifications can be made within the scope of the present invention.

FIG. 25 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source. The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 25 shows a circuit implementation for a system that transfers energy to the implanted energy components of the apparatus of the present invention from outside of the patient's body using inductive energy transfer. An inductive energy transfer system typically uses an external transmitting coil and an internal receiving coil. The receiving coil, L1, is included in the schematic FIG. 3; the transmitting parts of the system are excluded.

The implementation of the general concept of energy balance and the way the information is transmitted to the external energy transmitter can of course be implemented in numerous different ways. The schematic FIG. 25 and the above described method of evaluating and transmitting the information should only be regarded as examples of how to implement the control system.

Circuit Details

In FIG. 25 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 1006 of FIG. 8 could be incorporated in any of the embodiments of FIGS. 11-17, the hydraulic valve shifting device 1014 of FIG. 11 could be incorporated in the embodiment of FIG. 10, and the gear box 1024 could be incorporated in the embodiment of FIG. 9. Please observe that the switch simply could mean any electronic circuit or component.

The embodiments described in connection with FIGS. 22, 24 and 25 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises an external control unit for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto. The system further comprises a determination device adapted to determine an energy balance between the energy received by the internal energy receiver and the energy used for the implantable energy consuming components of the apparatus, wherein the external control unit controls the transmission of wireless energy from the external energy-transmission device, based on the energy balance determined by the determination device.

Further, the system may comprise any of the following:

A primary coil in the external energy source adapted to transmit the wireless energy inductively to a secondary coil in the internal energy receiver.

The determination device is adapted to detect a change in the energy balance, and the external control unit controls the transmission of wireless energy based on the detected energy balance change The determination device is adapted to detect a difference between energy received by the internal energy receiver and energy used for the implantable energy consuming components of the apparatus, and the external control unit controls the transmission of wireless energy based on the detected energy difference.

The external control unit controls the external energy-transmission device to decrease the amount of transmitted wireless energy if the detected energy balance change implies that the energy balance is increasing, or vice versa, wherein the decrease/increase of energy transmission corresponds to a detected change rate.

The external control unit controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

FIGS. 26-29 show in more detail block diagrams of four different ways of hydraulically or pneumatically powering an implanted apparatus according to the invention.

Figure 26:
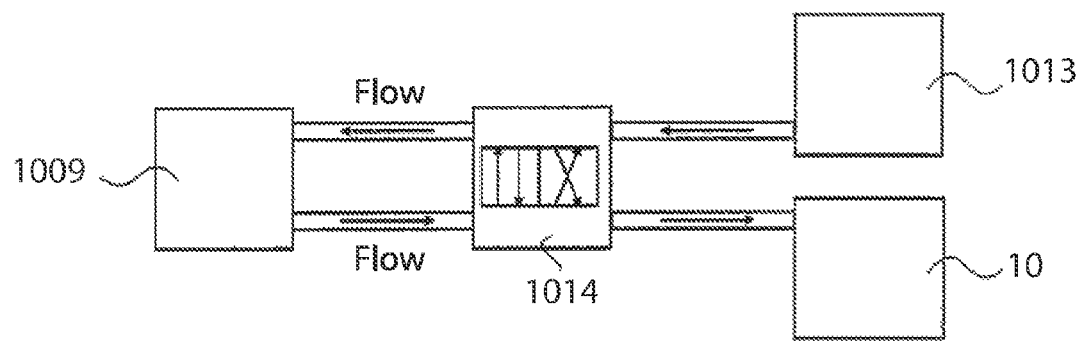

FIG. 26 shows a system as described above with. The system comprises an implanted apparatus 10 and further a separate regulation reservoir 1013, a one way pump 1009 and an alternate valve 1014.

Figure 27:
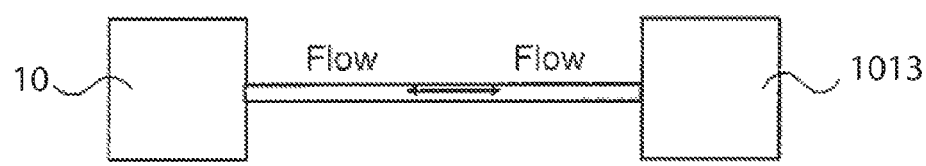

FIG. 27 shows the apparatus 10 and a fluid reservoir 1013. By moving the wall of the regulation reservoir or changing the size of the same in any other different way, the adjustment of the apparatus may be performed without any valve, just free passage of fluid any time by moving the reservoir wall.

Figure 28:
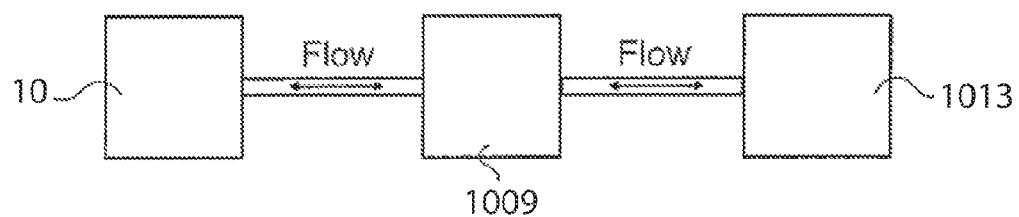

FIG. 28 shows the apparatus 10, a two way pump 1009 and the regulation reservoir 1013.

Figure 29:
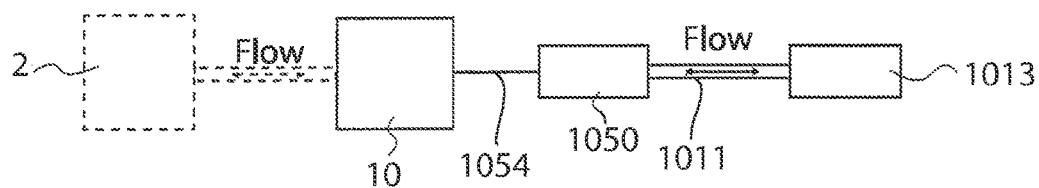
Figure 30:
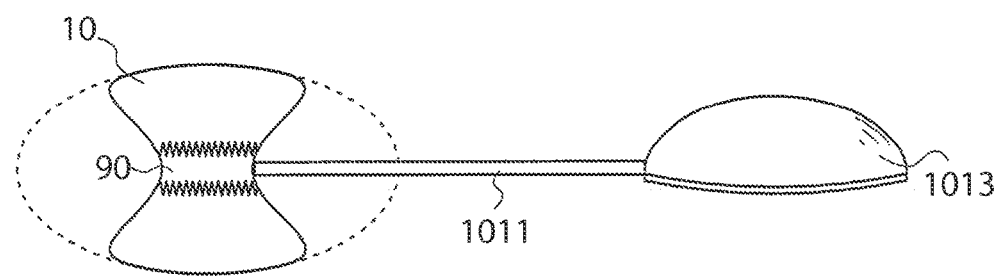
Figure 30:
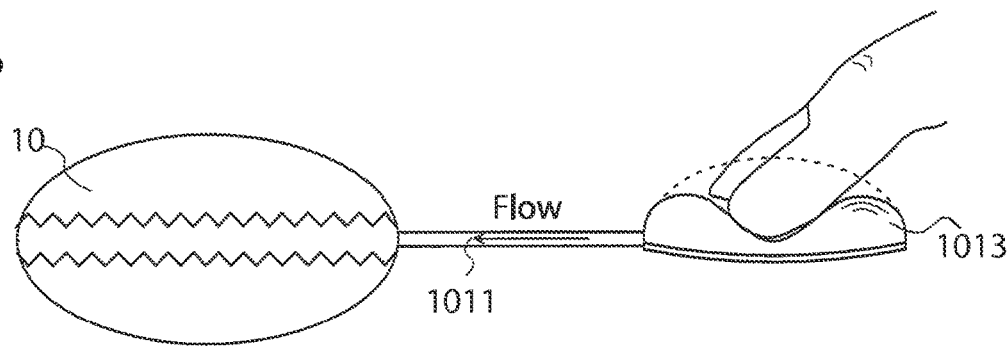
Figure 30:
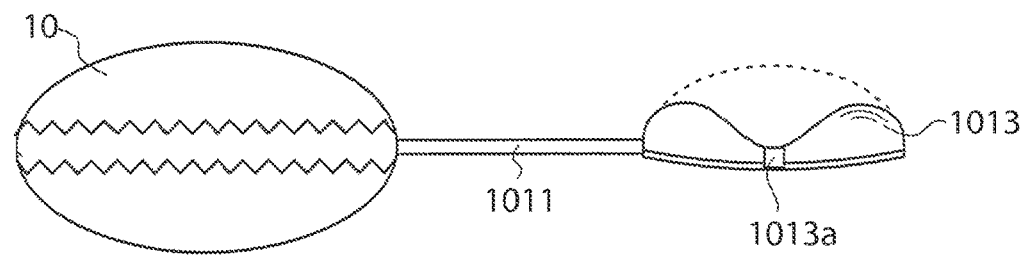
Figure 31:
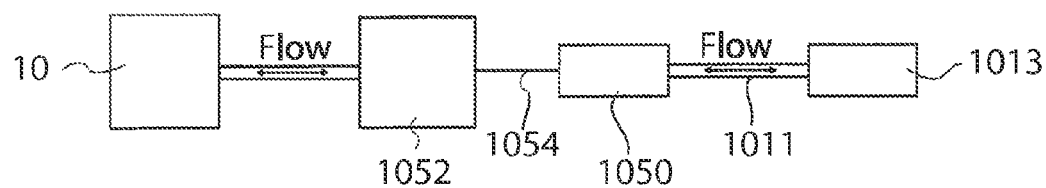
Figure 32:
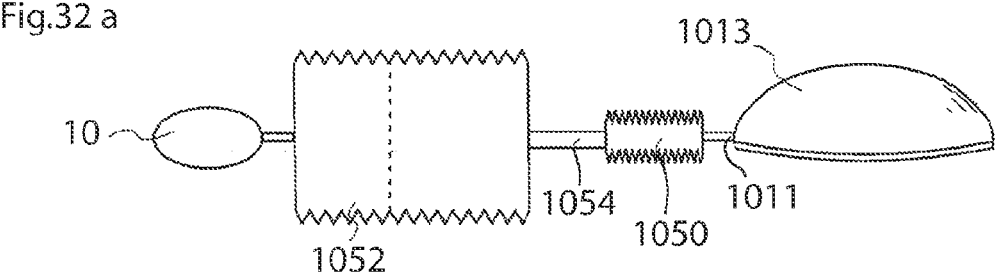
Figure 32:
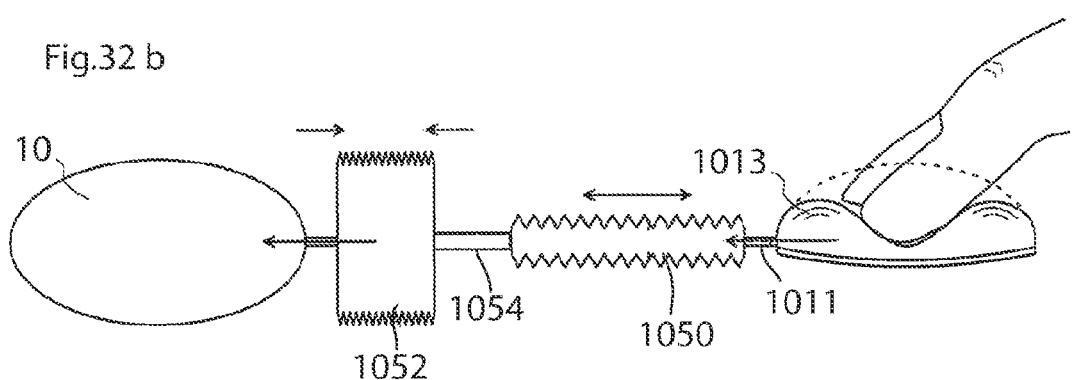
Figure 32:
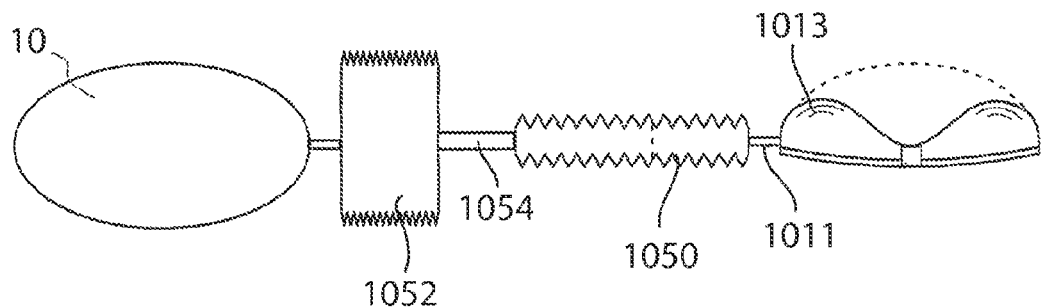

FIG. 29 shows a block diagram of a reversed servo system with a first closed system controlling a second closed system. The servo system comprises a regulation reservoir 1013 and a servo reservoir 1050. The servo reservoir 1050 mechanically controls an implanted apparatus 10 via a mechanical interconnection 1054. The apparatus has an expandable/contactable cavity. This cavity is preferably expanded or contracted by supplying hydraulic fluid from the larger adjustable reservoir 1052 in fluid connection with the apparatus 10. Alternatively, the cavity contains compressible gas, which can be compressed and expanded under the control of the servo reservoir 1050.

The servo reservoir 1050 can also be part of the apparatus itself.

In one embodiment, the regulation reservoir is placed subcutaneous under the patient's skin and is operated by pushing the outer surface thereof by means of a finger. This system is illustrated in FIGS. 30a-c. In FIG. 30a, a flexible subcutaneous regulation reservoir 1013 is shown connected to a bulge shaped servo reservoir 1050 by means of a conduit 1011. This bellow shaped servo reservoir 1050 is comprised in a flexible apparatus 10. In the state shown in FIG. 25, the servo reservoir 1050 contains a minimum of fluid and most fluid is found in the regulation reservoir 1013. Due to the mechanical interconnection between the servo reservoir 1050 and the apparatus 10, the outer shape of the apparatus 10 is contracted, i.e., it occupies less than its maximum volume. This maximum volume is shown with dashed lines in the figure.

FIG. 30b shows a state wherein a user, such as the patient in with the apparatus is implanted, presses the regulation reservoir 1013 so that fluid contained therein is brought to flow through the conduit 1011 and into the servo reservoir 1050, which, thanks to its bellow shape, expands longitudinally. This expansion in turn expands the apparatus 10 so that it occupies its maximum volume, thereby stretching the stomach wall (not shown), which it contacts.

The regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

An alternative embodiment of hydraulic or pneumatic operation will now be described with reference to FIGS. 31 and 32a-c. The block diagram shown in FIG. 31 comprises with a first closed system controlling a second closed system. The first system comprises a regulation reservoir 1013 and a servo reservoir 1050. The servo reservoir 1050 mechanically controls a larger adjustable reservoir 1052 via a mechanical interconnection 1054. An implanted apparatus 10 having an expandable/contactable cavity is in turn controlled by the larger adjustable reservoir 1052 by supply of hydraulic fluid from the larger adjustable reservoir 1052 in fluid connection with the apparatus 10.

An example of this embodiment will now be described with reference to FIG. 32a-c. Like in the previous embodiment, the regulation reservoir is placed subcutaneous under the patient's skin and is operated by pushing the outer surface thereof by means of a finger. The regulation reservoir 1013 is in fluid connection with a bellow shaped servo reservoir 1050 by means of a conduit 1011. In the first closed system 1013, 1011, 1050 shown in FIG. 31a, the servo reservoir 1050 contains a minimum of fluid and most fluid is found in the regulation reservoir 1013.

The servo reservoir 1050 is mechanically connected to a larger adjustable reservoir 1052, in this example also having a bellow shape but with a larger diameter than the servo reservoir 1050. The larger adjustable reservoir 1052 is in fluid connection with the apparatus 10. This means that when a user pushes the regulation reservoir 1013, thereby displacing fluid from the regulation reservoir 1013 to the servo reservoir 1050, the expansion of the servo reservoir 1050 will displace a larger volume of fluid from the larger adjustable reservoir 1052 to the apparatus 10. In other words, in this reversed servo, a small volume in the regulation reservoir is compressed with a higher force and this creates a movement of a larger total area with less force per area unit.

Like in the previous embodiment described above with reference to FIGS. 32a-c, the regulation reservoir 1013 is preferably provided with means 1013a for keeping its shape after compression. This means, which is schematically shown in the figure, will thus keep the apparatus 10 in a stretched position also when the user releases the regulation reservoir. In this way, the regulation reservoir essentially operates as an on/off switch for the system.

The invention claimed is:

1. An apparatus for treating a urinary retention of a patient by discharging urine from a mammal urinary bladder through a mammal urethra, comprising:
an expandable member adapted to be implanted inside the urinary bladder of the patient,
a detachable coupling adapted to be implanted inside the urinary bladder of the patient, and
a control device adapted to control the emptying of a non-functioning mammal urinary bladder for treating the urinary retention, to control a volume of the expandable member, and to be connected to the expandable member through a wall of the urinary bladder,
wherein the expandable member is configured to:
as a result of its expansion in volume, discharge urine from the urinary bladder, and
be releasably attached to the control device via the detachable coupling,
wherein:
a first mating part of the detachable coupling is arranged in a proximal part of the expandable member and to fit with a second mating part of the detachable coupling, the second mating part being attached to the control device in order to establish a detachable coupling between the expandable member and the control device,
the expandable member is connected or connectable to the control device via an interconnecting device adapted to go through said wall of the urinary bladder through a surgically performed hole in said urinary wall and further adapted to be placed in a sutured tunnel onto the urinary bladder in close relation to the hole adapted to seal the hole,
the interconnecting device is further adapted to be releasably connected to the expandable member inside the urinary bladder,
the expandable member is replaceable by being adapted to assume a shape which admits transportation through the urethra, and wherein
said detachable coupling is adapted to be placed between the interconnecting device and the expandable member and to be detachable by an instrument introduced through the urethra.

2. An apparatus according to claim 1, wherein the control device comprises an internal control unit comprising at least one of a subcutaneously placed switch, an electronic circuit, a motor or a pump, wherein said internal control unit is operable from outside of the patient's body.

3. An apparatus according to claim 1, wherein:
the expandable member is hydraulically controlled and comprises a cavity for hydraulic fluid;
the control device comprises an implantable bladder operating reservoir for hydraulic fluid, and wherein
the expandable member and the control device are adapted to be hydraulically connected through the wall of the urinary bladder via the interconnecting device, wherein the interconnecting device comprises an implantable tube to establish hydraulic connection and for transporting the hydraulic fluid between the bladder operating reservoir and the cavity.

4. An apparatus according to claim 3, wherein the detachable coupling is adapted to be connected to the hydraulic connection to transport hydraulic fluid to and from the bladder operating reservoir and the expandable member.

5. An apparatus according to claim 3, wherein the expandable member is adapted to be emptied by a pressure exerted by urine of the urinary bladder to transport the hydraulic fluid from the cavity to the bladder operating reservoir.

6. An apparatus according to claim 3, wherein the control device comprises an implantable operation device for transporting hydraulic fluid to and from the cavity and the bladder operating reservoir, wherein the operation device is capable of transporting hydraulic fluid to the cavity of the expandable member to obtain a suitable urinary pressure for discharging urine.

7. An apparatus according to claim 6, wherein the operation device is capable of transporting hydraulic fluid to the cavity of the expandable member to obtain a urinary pressure of at least 50 cm water pressure for discharging urine.

8. An apparatus according to claim 6, wherein the operation device is a powered pump.

9. An apparatus according to claim 6, wherein the operation device comprises an injection port adapted to at least one of; calibrate the amount of hydraulic fluid and manually operating, by said injection port operated from outside a body, for filling or emptying said injection port.

10. An apparatus according to claim 6, wherein the hydraulic fluid comprises an agent for counteracting microbial growth.

11. An apparatus according to claim 10, further comprising implantable restriction devices adapted to close each ureter of a patient when discharging urine from the urinary bladder.

12. An apparatus according to claim 11, wherein the restriction devices adapted to open and close the ureters are hydraulically operable by hydraulic fluid.

13. An apparatus according to claim 12, wherein the operating hydraulic fluid is displaced from the bladder operating reservoir, wherein the restriction devices open and close by the operation device.

14. An apparatus according to claim 12, comprising a second reservoir, wherein the operating hydraulic fluid is displaced from said second reservoir.

15. An apparatus according to claim 3, wherein the expandable member is adapted to be emptied by at least one of; a pressure exerted by urine of the urinary bladder to transport the hydraulic fluid from the cavity to the bladder operating reservoir, and a pressure exerted by urine of the urinary bladder to transport the hydraulic fluid from the cavity to the bladder operating reservoir by a second connection between the expandable member and the bladder operating reservoir, sized such that a pumps pumping volume capacity is significantly much larger than an emptying capacity of said second connection, when open, wherein the expandable member is adapted to be emptied by the pressure exerted by urine of the urinary bladder to transport the hydraulic fluid from the cavity to the bladder operating reservoir by said second connection.

16. An apparatus according to claim 1, comprising a restriction device adapted to open and close the urethra.

17. An apparatus according to claim 1, wherein the control device further comprises an implantable device for electrically stimulating muscles of the urinary bladder to contract the same, to co-operate with the expandable member to discharge urine from the urine bladder, wherein the electrically stimulating device comprises a plurality of electrode strips adapted to be attached to muscles of the urinary bladder.

18. An apparatus according to claim 1, adapted to be included in a system, comprising, at least one of; at least one switch implantable in the patient, a wireless remote control, and an implantable hydraulic reservoir hydraulically connected to the apparatus adapted to be regulated by manually pressing the hydraulic reservoir and adapted to manually and non-invasively control the apparatus.

19. An apparatus according to claim 1, adapted to be included in a system, comprising an internal energy receiver, adapted to be energised non-invasively and wirelessly by an energy transmission device from outside the patient's body, adapted to send wireless energy to at least one of:
   an implantable internal energy source, chargeable by the energy transferred from the energy transmission device in a wireless mode, and
   at least one implantable energy consuming component of the apparatus, energized with wireless energy.

20. An apparatus according to claim 1, adapted to be included in a system, comprising a sensor, a measuring device, or a sensor and a measuring device, sensing or measuring at least one of:
   at least one physical parameter of the patient, comprising at least one of; a urinary pressure in the urinary bladder directly or indirectly including measuring when the sensor is an implantable pressure sensor, the pressure inside an implantable member and any other physical parameter of the patient, and
   at least one functional parameter related to the apparatus, wherein
   the apparatus further comprising a feedback device for sending feedback information from inside the patient's body to at least one of; an implantable internal control unit then comprised and the outside of the patient's body, wherein the feedback information being related to at least one of; the at least one physical parameter of the patient and the at least one functional parameter related to the apparatus.

21. An expandable member comprising a detachable coupling, the expandable member and the detachable coupling being adapted to be implanted inside a urinary bladder of a patent, wherein:
   the expandable member is adapted to be releasably attached to a control device via the detachable coupling, wherein the control device is adapted to control a volume of the expandable member and to be connected to the expandable member through a wall of the urinary bladder;
   the detachable coupling comprises a first mating part and a second mating part;
   the first mating part is arranged in a proximal part of the expandable member and to fit with the second mating part;
   the second mating part is adapted to be attached to the control device in order to establish a detachable coupling between the expandable member and the control device;
   the expandable member is connected or connectable to the control device via an interconnecting device adapted to go through said wall of the urinary bladder through a surgically performed hole in said urinary wall and further adapted to be placed in a sutured tunnel onto the urinary bladder in close relation to the hole adapted to seal the hole;
   the interconnecting device is further adapted to be releasably connected to the expandable member inside the urinary bladder;
   the expandable member is replaceable by being adapted to assume a shape which admits transportation through the urethra, and
   said detachable coupling is adapted to be placed between the interconnecting device and the expandable member and to be detachable by an instrument introduced through the urethra.

* * * * *